US012779422B2

(12) United States Patent
Cui et al.

(10) Patent No.: US 12,779,422 B2
(45) Date of Patent: Nov. 3, 2026

(54) SYSTEMS AND METHODS FOR CRACKING HYDROCARBONS TO PRODUCE LIGHT OLEFINS

(71) Applicants: King Abdullah University of Science and Technology, Thuwal (SA); Saudi Arabian Oil Company, Dhahran (SA)

(72) Inventors: Mengmeng Cui, Thuwal (SA); Pedro Castano, Thuwal (SA); Juan Manuel Colom, Thuwal (SA); Jorge Gascon Sabate, Thuwal (SA); Khalid Ali Almajnouni, Jeddah (SA); Lujain R. Alfilfil, Thuwal (SA)

(73) Assignees: King Abdullah University of Science and Technology, Thuwal (SA); Saudi Arabian Oil Company, Dhahran (SA)

( * ) Notice: Subject to any disclaimer, the term of this patent is extended or adjusted under 35 U.S.C. 154(b) by 257 days.

(21) Appl. No.: 18/425,872

(22) Filed: Jan. 29, 2024

(65) Prior Publication Data

US 2025/0242321 A1 Jul. 31, 2025

(51) Int. Cl.
*C07C 4/06* (2006.01)
*B01D 3/34* (2006.01)
(Continued)

(52) U.S. Cl.
CPC .............. *B01J 8/008* (2013.01); *B01D 3/346* (2013.01); *B01J 4/001* (2013.01); *B01J 8/1818* (2013.01);
(Continued)

(58) Field of Classification Search
CPC ........ B01J 8/008; B01J 8/1818; B01J 8/1872; B01J 8/24; B01J 4/001; B01J 2208/00769;
(Continued)

(56) References Cited

U.S. PATENT DOCUMENTS

| | | | |
|---|---|---|---|
| 2,348,699 | A | 5/1944 | Tuttle |
| 2,429,359 | A | 10/1947 | Kassel |

(Continued)

FOREIGN PATENT DOCUMENTS

| | | | |
|---|---|---|---|
| CN | 102086402 | A | 6/2011 |
| CN | 10873356 | A | 11/2018 |

(Continued)

OTHER PUBLICATIONS

Search Report pertaining to International Application No. PCT/US2021/036336 dated Oct. 5, 2021, 16 pages.

(Continued)

*Primary Examiner* — In Suk C Bullock
*Assistant Examiner* — Jason Y CHong
(74) *Attorney, Agent, or Firm* — Dinsmore & Shohl LLP

(57) ABSTRACT

Systems and processes for cracking hydrocarbons to produce light olefins include an FCC reactor utilizing counter-current flow that includes a reaction zone comprising an elongated reaction tube that has a feed inlet, a product outlet, and a catalyst inlet. In embodiments, the FCC reactor further includes a freeboard zone. The freeboard zone is configured to reduce a superficial velocity of the cracked hydrocarbon fluids in the reaction zone, causing catalyst entrained in the cracked hydrocarbon fluids to at least partially separate from the cracked hydrocarbon fluids. In embodiments, the FCC reactor includes a dense fluidized bed unit. The dense fluidized bed unit is configured to inject a fluidizing gas such that bubbles are formed within the solid particles of the dense fluidized bed of solid particles, which causes the catalyst to overflow from the dense fluidized bed of solid particles into the reaction zone.

13 Claims, 7 Drawing Sheets

(51) Int. Cl.

| | |
|---|---|
| ***B01J 4/00*** | (2006.01) |
| ***B01J 8/00*** | (2006.01) |
| ***B01J 8/18*** | (2006.01) |
| ***B01J 8/24*** | (2006.01) |
| ***C10G 11/18*** | (2006.01) |

(52) U.S. Cl.
CPC ............... *B01J 8/1872* (2013.01); *B01J 8/24* (2013.01); *C07C 4/06* (2013.01); *B01J 2208/00769* (2013.01); *B01J 2208/0092* (2013.01); *B01J 2208/06* (2013.01)

(58) Field of Classification Search
CPC .......... B01J 2208/0092; B01J 2208/06; B01D 3/346; C07C 4/06; C10G 11/18; C10G 11/182
See application file for complete search history.

(56) References Cited

U.S. PATENT DOCUMENTS

| | | | |
|---|---|---|---|
| 2,561,334 | A | 7/1951 | Bowles et al. |
| 2,685,498 | A | 8/1954 | Dickinson |
| 2,862,871 | A | 12/1958 | Smith |
| 2,882,206 | A | 4/1959 | Martin et al. |
| 2,929,774 | A | 3/1960 | Smith |
| 3,498,907 | A | 3/1970 | Doelp, Jr. et al. |
| 3,551,513 | A | 12/1970 | Yuichi et al. |
| 3,650,946 | A | 3/1972 | Mourning |
| 3,708,552 | A | 1/1973 | Kunii et al. |
| 3,799,868 | A | 3/1974 | Gantt |
| 3,799,886 | A | 3/1974 | Felice et al. |
| 3,837,822 | A | 9/1974 | Ward |
| 3,879,281 | A | 4/1975 | Jones et al. |
| 4,087,350 | A | 5/1978 | Kolombos et al. |
| 4,247,987 | A | 2/1981 | Coulaloglou et al. |
| 4,259,175 | A | 3/1981 | Mcarthur |
| 4,340,465 | A | 7/1982 | Miller et al. |
| 4,356,082 | A | 10/1982 | Gross |
| 4,552,645 | A | 11/1985 | Gartside et al. |
| 4,820,493 | A | 4/1989 | Haddad et al. |
| 5,062,944 | A | 11/1991 | Leib et al. |
| 5,196,172 | A | 3/1993 | Weinberg et al. |
| 5,451,313 | A | 9/1995 | Wegerer et al. |
| 5,462,652 | A | 10/1995 | Wegerer |
| 5,468,369 | A | 11/1995 | Muldowney |
| 5,944,982 | A | 8/1999 | Lomas |
| 6,656,346 | B2 | 12/2003 | Ino et al. |
| 6,869,521 | B2 | 3/2005 | Lomas |
| 7,077,949 | B2 | 7/2006 | Bakker et al. |
| 7,425,258 | B2 | 9/2008 | Chen et al. |
| 7,479,218 | B2 | 1/2009 | Letzsch |
| 7,594,994 | B1 | 9/2009 | Seibert et al. |
| 7,658,837 | B2 | 2/2010 | Soares Cerqueira et al. |
| 8,349,170 | B2 | 1/2013 | Tammera et al. |
| 9,388,095 | B2 | 7/2016 | Leroy et al. |
| 9,452,404 | B2 | 9/2016 | Marri et al. |
| 9,458,394 | B2 | 10/2016 | Dean et al. |
| 9,771,530 | B2 | 9/2017 | Sayed et al. |
| 2003/0194360 | A1 | 10/2003 | Huziwara et al. |
| 2004/0024276 | A1 | 2/2004 | Smith et al. |
| 2004/0065591 | A1 | 4/2004 | Rockwell |
| 2004/0104148 | A1 | 6/2004 | Lomas et al. |
| 2004/0124124 | A1 | 7/2004 | Moreira Assumpcao et al. |
| 2007/0205139 | A1 | 9/2007 | Kulprathipanja et al. |
| 2008/0035526 | A1 | 2/2008 | Hedrick et al. |
| 2011/0108458 | A1 | 5/2011 | Leonard et al. |
| 2012/0291340 | A1 | 11/2012 | Boon et al. |
| 2013/0338418 | A1 | 12/2013 | Xu et al. |
| 2014/0014555 | A1 | 1/2014 | Marri et al. |
| 2014/0142362 | A1 | 5/2014 | Davydov et al. |
| 2016/0160134 | A1 | 6/2016 | Voolapalli et al. |
| 2019/0316041 | A1 | 10/2019 | Tian et al. |
| 2019/0316047 | A1 | 10/2019 | Al-Majnouni et al. |
| 2021/0179514 | A1 | 6/2021 | Thinon et al. |
| 2021/0317373 | A1 | 10/2021 | Gong et al. |

FOREIGN PATENT DOCUMENTS

| | | | |
|---|---|---|---|
| CN | 109666505 | A | 4/2019 |
| CN | 10540860 | A | 12/2019 |
| CN | 10540861 | A | 12/2019 |
| WO | 0179392 | A2 | 10/2001 |
| WO | 2013089885 | A1 | 6/2013 |
| WO | 2014011759 | A1 | 1/2014 |
| WO | 2018169768 | A1 | 9/2018 |
| WO | 2020109885 | A1 | 6/2020 |
| WO | 2021019465 | A1 | 2/2021 |

OTHER PUBLICATIONS

Search Report pertaining to International Application No. PCT/US2022/051206 dated Mar. 15, 2023, 13 pages.

Alabdullah et al., "One-step conversion of crude oil to light olefins using a multi-zone reactor", Nature Catalysis, vol. 4, pp. 233-241, Mar. 2021.

Corma et al., "Crude oil to chemicals: light olefins from crude oil", The Royal Society of Chemistry, Catalysis Science & Technology, vol. 7, pp. 12-46, 2017.

Dupain et al., "Optimal conditions in fluid catalytic cracking: A mechanistic approach", Applied Catalysis A: General, vol. 297, pp. 198-219, 2006.

Parthasarathi et al., "HS-FCC High-severity fluidized catalytic racking: a newcomer to the FCC family", Appl Petrochem Res, vol. 4, pp. 441-444, 2014.

First Substantive Examination Report dated Jul. 5, 2026, pertaining to SA Patent Application No. 1020250556, 9 pgs.

SYSTEMS AND METHODS FOR CRACKING HYDROCARBONS TO PRODUCE LIGHT OLEFINS

TECHNICAL FIELD

Embodiments of the present disclosure generally relate to systems and processes for producing olefins from hydrocarbon feed compositions, in particular, systems and processes for counter-current reactors for producing olefins.

BACKGROUND

Light olefins, such as ethylene, propene, butene, butadiene, and aromatic compounds such as benzene, toluene and xylenes are basic intermediates for the petrochemical industry. These compounds are produced through refinery fluidized catalytic cracking (FCC) processes. The worldwide increasing demand for light olefins and aromatics remains a major challenge for many integrated refineries. In particular, the production of some valuable light olefins such as ethylene, propene, and butene has attracted increased attention as purified olefin streams are considered the building blocks for polymer synthesis. The production of light olefins depends on several process variables, such as the feed type, operating conditions, and the type of catalyst. To match the increasing need for light olefins, there is a need for improved methods to produce light olefins.

SUMMARY

Conventional fluidized catalytic cracking processes typically utilize co-current flow patterns whereby the catalyst and hydrocarbons flow through the reactor in the same direction, which can result in undesirable flow patterns such as back-mixing and core-annular flow. Embodiments of the present disclosure are directed to methods to produce light olefins by catalytic cracking, where the catalyst and hydrocarbons contact each other in a counter-current manner with increased solid holdup in the reaction zone. Counter-current flow may be desirable to increase the conversion of the feed. For example, during counter-current flow, fresh catalyst may move from the top of the reactor to the bottom of the reactor while hydrocarbon feed flows from the bottom to the top of the reactor. The spent catalyst at the bottom of the reactor and nearing the exit of the reactor contacts with the fresh feed flowing upward and converts the reactive components in the feed. The less reactive components in the feed are converted as the feed travels upward, contacting the hot and fresh catalyst in the top section of the reactor. Counter-current flow between the hydrocarbons and catalyst may prevent back-mixing or core-annular flow, which often lead to a reduced yield of light olefins in traditional riser reactors where the catalyst and hydrocarbons flow through the reactor co-currently. Additionally, the increase in solid holdup is preferable to enhance interphase heat transfer and catalytic reactions in the counter-current flow. The increase may be achievable with a freeboard zone or the addition of a dense fluidized bed at the top of the counter-current reactor to aid in distributing the catalyst into the reactor with stable but adjustable solid flux and perform possible cracking reactions with another stream of hydrocarbon feed. The counter-current flow and freeboard zone may achieve at least 60 wt. % conversion of crude oil to light olefins based on the total flow rate of the crude oil feed.

According to embodiments, a fluidized catalytic cracking (FCC) system for fluidized catalytic cracking of hydrocarbons to produce light olefins includes an FCC reactor and a catalyst regenerator. The FCC reactor includes a reaction zone having an elongated reaction tube that is vertically oriented and has a top end and a bottom end, a feed inlet proximate the bottom end of the reaction zone, a product outlet proximate a top end of the reaction zone, a catalyst inlet proximate the top end of the reaction zone, a stripping unit disposed axially below the feed inlet and in fluid communication with the bottom end of the reaction zone, the stripping unit comprising a steam inlet and a catalyst outlet, and a freeboard zone disposed axially above the catalyst inlet and in fluid communication with the top end of the reaction zone. The reactor system is configured to introduce a hydrocarbon feed to the reaction zone through the feed inlet and a catalyst to the reaction zone through the catalyst inlet such that the catalyst contacts the hydrocarbon feed to produce cracked hydrocarbon fluids, and the cracked hydrocarbon fluids have a net upward superficial velocity through the reaction zone. The catalyst has a net downward superficial velocity through the reaction zone, and the net downward superficial velocity of the catalyst is counter-current relative to the net upward superficial velocity of the cracked hydrocarbon fluids. The freeboard zone is configured to reduce a superficial velocity of the cracked hydrocarbon fluids at the top end of the reaction zone, which causes catalyst entrained in the cracked hydrocarbon fluids to fall back to the top end of the reaction zone, thereby separating at least a portion of entrained catalyst from the cracked hydrocarbon fluids.

According to embodiments, a fluidized catalytic cracking (FCC) system for fluidized catalytic cracking of hydrocarbons to produce light olefins includes an FCC reactor and a catalyst regenerator. The FCC reactor includes a reaction zone having an elongated reaction tube that is vertically oriented and has a top end and a bottom end, a feed inlet proximate the bottom end of the reaction zone, a catalyst inlet proximate a top end of the reaction zone, a stripping unit disposed axially below the feed inlet and in fluid communication with the bottom end of the reaction zone, the stripping unit comprising a steam inlet and a catalyst outlet, and a dense fluidized bed unit comprising a vessel enclosing the top end of the elongated reaction tube. The catalyst in the vessel forms a dense fluidized bed of solid particles. The FCC reactor is configured to introduce a hydrocarbon feed to the reaction zone through the feed inlet and a catalyst to the reaction zone through the catalyst inlet such that the catalyst contacts the hydrocarbon feed to produce cracked hydrocarbon fluids, wherein the catalyst include solid particles. The cracked hydrocarbon fluids have a net upward superficial velocity through the reaction zone. The catalyst include solid particles and has a net downward superficial velocity through the reaction zone. The net downward superficial velocity of the catalyst is counter-current relative to the net upward superficial velocity of the hydrocarbons. The dense fluidized bed unit is configured to inject a fluidizing gas such that bubbles are formed within the solid particles of the dense fluidized bed of solid particles, which causes the catalyst to overflow from the dense fluidized bed of solid particles into the reaction zone.

According to embodiments, a method for cracking hydrocarbons to produce light olefins includes introducing a hydrocarbon feed into a feed inlet of a fluidized catalytic cracking (FCC) reactor and introducing a catalyst into a catalyst inlet of the FCC reactor. The FCC reactor includes a reaction zone comprising an elongated reaction tube that is vertically oriented and has a top end and a bottom end, a stripping unit disposed axially below the feed inlet and in fluid communication with the bottom end of the reaction zone, the stripping unit comprising a steam inlet and a catalyst outlet, and a freeboard zone disposed axially above the catalyst inlet and in fluid communication with the top end of the reaction zone. The method further includes contacting the catalyst with the hydrocarbon feed in the reaction zone to produce cracked hydrocarbon fluids and spent catalyst. The catalyst has a net downward superficial velocity through the reaction zone, and the cracked hydrocarbon fluids have a net upward superficial velocity through the reaction zone. The method further includes passing the cracked hydrocarbon fluids and at least a portion of the spent catalyst through the freeboard zone which is operable to reduce the superficial velocity of the spent catalyst such that a portion of the spent catalyst is at least partially separated from the hydrocarbon fluids to form an FCC effluent. The method further includes passing the FCC effluent out of the FCC reactor through a product outlet.

BRIEF DESCRIPTION OF THE DRAWINGS

The following detailed description of specific aspects of the present disclosure can be best understood when read in conjunction with the following drawings, in which like structure is indicated with like reference numerals and in which.

For purposes of describing the simplified schematic illustrations and descriptions in FIGS. 1-4, the numerous valves, temperature sensors, flow meters, pressure regulators, electronic controllers, pumps, heat exchangers, and the like that may be employed and well known to those of ordinary skill in the art of certain chemical processing operations may not be depicted. Further, accompanying components that are often included in typical chemical processing operations, such as valves, pipes, pumps, agitators, heat exchangers, condensers, boilers, instrumentation, internal vessel structures, or other subsystems may not be depicted. Though not depicted, it should be understood that these components are within the spirit and scope of the present embodiments disclosed. However, operational components, such as those described in the present disclosure, may be added to the embodiments described in this disclosure.

Reference will now be made in greater detail to various aspects of the present disclosure, some aspects of which are illustrated in the accompanying drawings.

DETAILED DESCRIPTION

Figure 1:
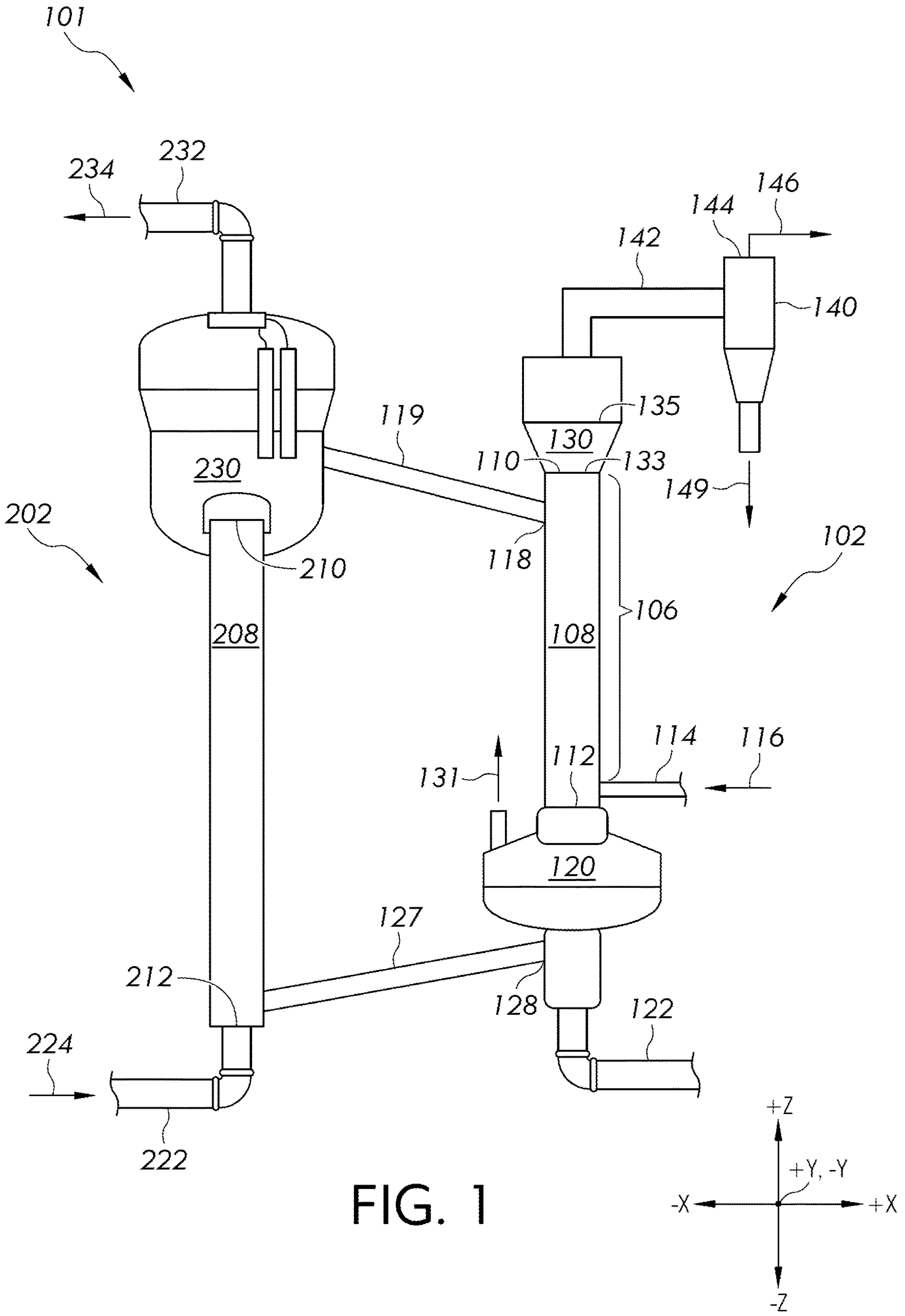
FIG. 1 schematically depicts an FCC system for producing light olefins, according to embodiments shown and described in the present disclosure.

The present disclosure is directed to systems and methods for cracking hydrocarbons to produce light olefins from a hydrocarbon feed in a fluidized catalytic cracking (FCC) system. Referring to FIG. 1, in embodiments, a system 101 for producing light olefins is depicted. The system 101 includes an FCC reactor 102 and a catalyst regenerator 202. The FCC reactor 102 may comprise a reaction zone 106 comprising an elongated reaction tube 108 that is vertically oriented (e.g., in the +/−Z direction of the coordinate axis in FIG. 1) and has a top end 110 and a bottom end 112. The FCC reactor 102 may further comprise a freeboard zone 130 disposed axially above the top end 110. The FCC reactor 102 may be operable to contact a hydrocarbon feed 116 with a catalyst at reaction temperatures sufficient to conduct cracking of the hydrocarbon feed 116. The freeboard zone 130 may be configured to reduce a superficial velocity of cracked hydrocarbon fluids at the top end 110 of the reaction zone 106, which may cause catalyst entrained in the cracked hydrocarbon fluids to fall back to the top end 110 of the reaction zone 106, thereby separating at least a portion of entrained catalyst from the cracked hydrocarbon fluids. The FCC reactor 102 may further include a cyclone 140 operable to separate catalyst fines from an FCC effluent 146.

Figure 2:
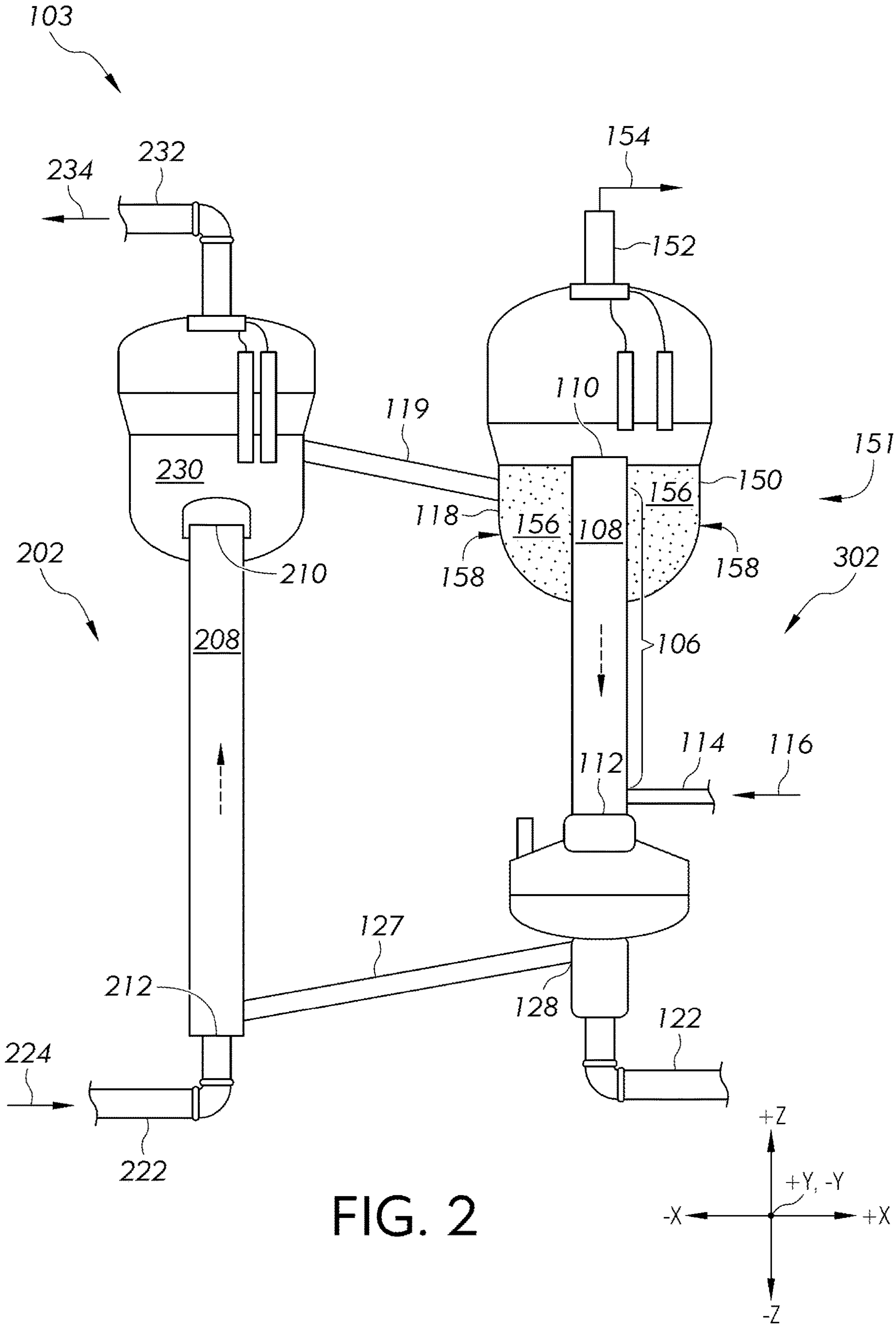
FIG. 2 schematically depicts another FCC system for producing light olefins, according to embodiments shown and described in the present disclosure.
Figure 3:
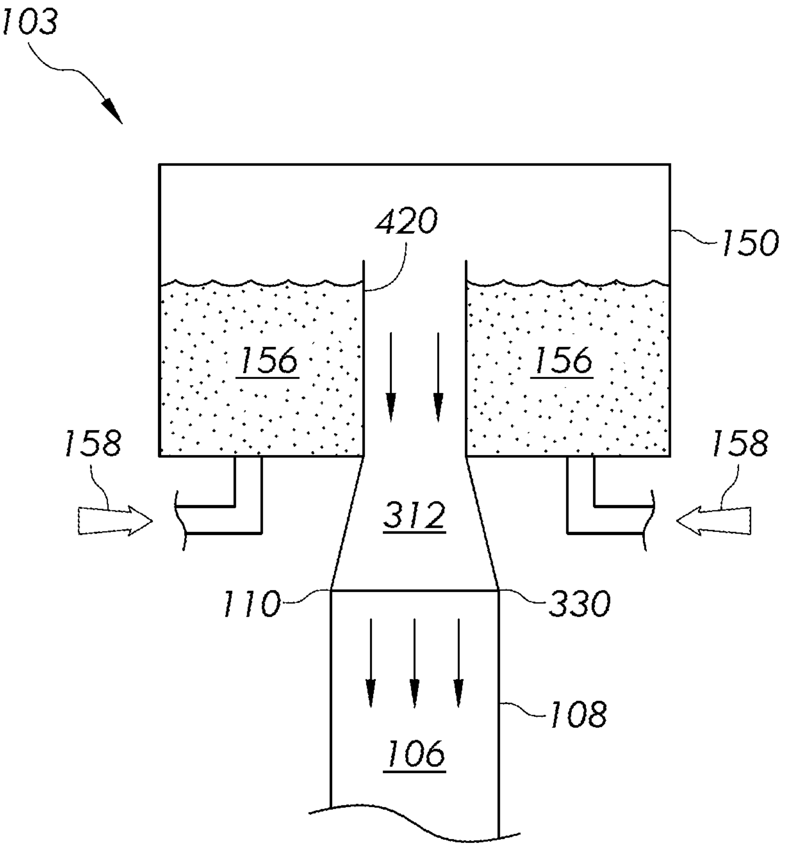
FIG. 3 schematically depicts a dense fluidized bed unit, according to embodiments shown and described in the present disclosure.

Referring to FIG. 2, in embodiments, a system 103 for producing light olefins is depicted. The system 103 includes an FCC reactor 102 and a catalyst regenerator 202. The FCC reactor 102 may comprise a reaction zone 106 comprising an elongated reaction tube 108 that is vertically oriented (e.g., in the +/−Z direction of the coordinate axis in FIG. 2) and has a top end 110 and a bottom end 112. The FCC reactor 102 may comprise a dense fluidized bed unit 150, which comprises a vessel 151 enclosing the top end 110 of the elongated reaction tube 108. The regenerated or fresh catalyst in the vessel 151 forms a dense fluidized bed 156. The FCC reactor 102 may be operable to contact a hydrocarbon feed 116 with a catalyst at reaction temperatures sufficient to conduct cracking of the hydrocarbon feed 116.

Referring back to FIG. 1, methods for cracking hydrocarbons to produce light olefins may include passing a hydrocarbon feed 116 through a feed inlet 114 to the reaction zone 106 and passing a catalyst through a catalyst inlet 118 to the reaction zone 106. The methods may further include contacting the catalyst and hydrocarbon feed 116 in the reaction zone 106 at reaction temperatures sufficient to produce cracked hydrocarbon fluids comprising one or more of ethylene, propylene, or butene. As the cracked hydrocarbon fluids and the catalyst move through the reaction zone 106, the hydrocarbon feed 116 may have a net upward superficial velocity through a horizontal cross-section of the elongated reaction tube 108, and the catalyst may have a net downward superficial velocity through a horizontal cross-section of the elongated reactor tube 108. The method may further include passing the cracked hydrocarbon fluids and at least a portion of the spent catalyst through the freeboard zone 130 which is operable to reduce the superficial velocity of the spent catalyst such that a portion of the spent catalyst is at least partially separated from the hydrocarbon fluids to form an FCC effluent 146. The method may further include passing the FCC effluent 146 out of the FCC reactor 102. The systems and methods of the present disclosure may increase the yield of light olefins such as ethylene, propylene, or butene from the FCC reactor 102 that includes a freeboard zone 130. Referring again to FIG. 2, methods for cracking hydrocarbons to produce light olefins may include passing a hydrocarbon feed 116 through a feed inlet 114 to the reaction zone 106 to be contacted by a catalyst passed into the reaction zone 106 by a dense fluidized bed unit 150. As the cracked hydrocarbon fluids pass through the reaction zone 106 to the product outlet 152, a portion of the cracked hydrocarbon fluids may be held up in the dense fluidized bed 156. Injection of the fluidizing gas 158 into the dense fluidized bed 156 may purge the cracked hydrocarbon fluids from the dense fluidized bed, effectively separating the cracked hydrocarbon fluids from the catalyst. The systems and methods of the present disclosure may increase the yield of light olefins such as ethylene, propylene, or butene from the FCC reactor 102 that includes a dense fluidized bed unit 150.

Embodiments of the present disclosure are directed to systems and processes for processing hydrocarbons to produce light olefins. Various embodiments are discussed herein. However, it should be understood that the forgoing detailed description section describes one or more specific embodiments and should not be viewed as limiting the scope of the appended claims.

The indefinite articles "a" and "an" are employed to describe elements and components of the present disclosure. The use of these articles means that one or at least one of these elements or components is present. Although these articles are conventionally employed to signify that the modified noun is a singular noun, as used herein the articles "a" and "an" also include the plural, unless otherwise stated in specific instances. Similarly, the definite article "the", as used in the present disclosure, also signifies that the modified noun may be singular or plural, unless otherwise stated in specific instances.

As used in this disclosure, passing a stream or effluent from one unit "directly" to another unit refers to passing the stream or effluent from the first unit to the second unit without passing the stream or effluent through an intervening reaction system or separation system that substantially changes the composition of the stream or effluent, such as through chemical reaction or through preferential separation of one or more constituents from the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent, unless otherwise specifically stated in the present disclosure. Combining two streams or effluents together upstream of a process unit also is not considered to comprise an intervening system that changes the composition of one or both of the streams or effluents being combined. Simply dividing a stream into two streams having the same composition is also not considered to comprise an intervening system that changes the composition of the stream.

As used in the present disclosure, the term "fluid" may be used to refer to a flowable composition that includes gases, liquids, or a combination of these.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. One or more "reaction zones" may be disposed in a reactor. As used in this disclosure, a "reaction zone" refers to an area where a particular reaction takes place in a reactor.

As used in this disclosure, the term "counter-current" may be used to describe the relationship between process streams flowing in substantially opposite directions where the process streams flow past or through one another. For example, a first process stream flowing in a substantially downward direction may flow counter-current to a second process stream flowing in a substantially upward direction. The direction of the flow of a stream may be in the same direction as the superficial velocity of that stream. As used throughout the present disclosure, the term "counter-current reactor" may be used to describe reactors in which catalyst and reactants and/or products flow through a reactor in a counter-current orientation.

As described herein, "superficial velocity" refers to the velocity at which an individual phase flows through a given cross-sectional area. The net flow of a phase is used to determine superficial velocity of that phase; thus, individual particles or molecules within a phase may move in a direction different from, or even opposite to, the net flow of a phase without affecting the direction of the superficial velocity of that phase. In embodiments, the superficial velocity of catalyst moving through the reaction zone may be in a substantially downward direction.

As used in this disclosure, a "catalyst" refers to any substance which increases the rate of a specific chemical reaction. Catalysts described in this disclosure may be utilized to promote various reactions, such as, but not limited to, cracking. As used in this disclosure, "cracking" generally refers to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used in this disclosure, the term "spent catalyst" refers to catalyst that has been contacted with reactants at reaction conditions in a reaction zone to catalyze a chemical reaction, but has not been subsequently regenerated in a regenerator or subjected to an in-place regeneration process in the reactor following contact with the reactants. The "spent catalyst" may have coke deposited on the catalyst and may include partially coked catalyst as well as fully coked catalysts. The amount of coke deposited on the "spent catalyst" may be greater than the amount of coke remaining on the regenerated catalyst following regeneration.

As used in this disclosure, the term "regenerated catalyst" refers to catalyst that has been contacted with reactants at reaction conditions in a reaction zone to catalyze a chemical reaction and then regenerated in a regenerator or subjected to an in-place regeneration process to heat the catalyst to a greater temperature, oxidize and remove at least a portion of the coke from the catalyst to restore at least a portion of the catalytic activity of the catalyst, or both. The "regenerated catalyst" may have less coke, a greater temperature, or both compared to spent catalyst and may have greater catalytic activity compared to spent catalyst. The "regenerated catalyst" may have more coke and lesser catalytic activity compared to fresh catalyst that has not passed through a cracking reaction zone and regenerator.

As used in this disclosure, the term "fresh catalyst" refers to catalyst that has not been previously contacted with reactants at reaction conditions in a reaction zone.

Referring again to FIG. 1, the FCC system 101 for cracking hydrocarbons to produce light olefins, such as ethylene, propylene, or butene, may include the FCC reactor 102 and the catalyst regenerator 202. The FCC reactor 102 may be operable to contact the hydrocarbon feed 116 with catalyst under reaction conditions sufficient to cause at least a portion of the hydrocarbon feed 116 to undergo cracking to produce light olefins. The catalyst regenerator 202 may be operable to regenerate spent catalyst into regenerated catalyst.

The hydrocarbon feed 116 may include a mixture of hydrocarbon materials. The hydrocarbon materials of the hydrocarbon feed 116 may include a crude oil or hydrocarbons derived from crude oil. As used in this disclosure, the term "crude oil" refers to a mixture of petroleum liquids and gases, including impurities such as sulfur-containing compounds, nitrogen-containing compounds and metal compounds, as distinguished from fractions of crude oil, such as fractions obtained from separating the crude oil by boiling point temperature. The hydrocarbon feed 116 may include, but may not be limited to, crude oil, vacuum residue, tar sands, bitumen, atmospheric residue, vacuum gas oils, demetalized oils, naphtha streams, gas condensate streams, or combinations of these materials. The hydrocarbon feed 116 may include one or a plurality of non-hydrocarbon constituents, such as one or more heavy metals, sulphur compounds, nitrogen compounds, inorganic components, or other non-hydrocarbon compounds. Crude oils contemplated herein include those having an API gravity of from 25° to 40°, such as from 25° to 30°, from 30° to 35°, from 35° to 40°, or any combination of these ranges. In embodiments, the hydrocarbon feed 116 may comprise a fraction of crude oil, or a petrochemical product formed from a crude oil, having an initial boiling point of at least 25° C. For example, in embodiments, the hydrocarbon feed 116 may comprise light naphtha and may have an initial boiling point from 25° C. to 35° C. and a final boiling point of from 85° C. to 95° C. In embodiments, the hydrocarbon feed 116 may comprise heavy naphtha and may have an initial boiling point from 80° C. to 95° C. and a final boiling point from 190° C. to 210° C. In further embodiments, the hydrocarbon feed 116 may comprise full range naphtha and have an initial boiling point from 25° C. to 35° C. and a final boiling point from 190° C. to 210° C.

In embodiments, the catalyst may comprise a zeolite catalyst, such as but not limited to a USY zeolite, a ZSM-5 zeolite, or a combination of multiple types of suitable zeolite catalysts. Alternatively or additionally, the catalyst may comprise other suitable solid acid catalysts. In embodiments, the catalyst may comprise fresh catalyst, regenerated catalyst, or combinations of fresh and regenerated catalyst as described in further detail herein. In embodiments, the catalyst may comprise binders, cracking promoters, inert fillers, matrix materials, or combinations of these to have acceptable physical and chemical properties to the catalyst, such as but not limited to catalyst attrition index and catalyst density, so that the catalyst can be used in the proposed reactor configuration.

The FCC reactor 102 may comprise a reaction zone 106 comprising an elongated reaction tube 108 that is vertically oriented and has a top end 110 and bottom end 112. As used herein, vertically oriented refers to the top end 110 and bottom end 112 of the elongated reaction tube 108 being disposed opposite each other in the axial direction (+/−Z direction in the coordinate axis of FIG. 1). The FCC reactor 102 may further comprise a feed inlet 114 proximate the bottom end 112 of the reaction zone 106. As described herein, proximate the bottom end 112 of the reaction zone 106 corresponds to positions that are a distance from the bottom end 112 of the reaction zone 106 that is less than 10% or less than 5% of a length of the elongated reaction tube 108. The FCC reactor 102 may further comprise a conduit 119 fluidly connecting the top end 110 of the reaction zone 106 with the catalyst regenerator 202 and catalyst inlet 118 proximate the top end 110 of the reaction zone 106. As described herein, proximate the top end 110 of the reaction zone 106 corresponds to positions that are a distance from the top end 110 of the reaction zone 106 that is less than 10% or less than 5% of a length of the elongated reaction tube 108. The FCC reactor 102 may be operable to contact the hydrocarbon feed 116 with the cracking catalyst at reaction conditions, which may cause hydrocarbons in the hydrocarbon feed 116 to undergo cracking reactions to produce light olefins, light aromatic compounds, or both.

The FCC reactor 102 may further comprise a stripping unit 120 disposed axially below the feed inlet 114 (below the feed inlet 114 in the −Z direction of the coordinate axis in FIG. 1) and in fluid communication with the bottom end 112 of the reaction zone 106. The stripping unit 120 may comprise a steam inlet 122, outlet 131, a conduit 127 fluidly connecting the stripping unit 120 and the catalyst regenerator 202, and a catalyst outlet 128 in fluid communication with the conduit 127. The stripping unit 120 may be operable to contact the used cracking catalyst with steam to strip any residual hydrocarbons (reaction products or unreacted feed hydrocarbons) from the used cracking catalyst prior to regenerating the used cracking catalyst.

The FCC reactor 102 may further comprise a freeboard zone 130 disposed axially above the catalyst inlet 118 and in fluid communication with the top end 110 of the reaction zone 106. The freeboard zone 130 may allow for the disengagement of product vapor from the catalyst particles. As the vapor and catalyst particles suspended therein enter the freeboard zone 130, the vapor continues to rise due to its upward superficial velocity, while any of the catalyst that is entrained in the vapor phase may fall due the greater density of the catalyst and also due to the decrease in the upward superficial velocity of the vapors in the freeboard zone 130. The freeboard zone 130 may decrease the superficial velocity of the vapor phase to a superficial velocity at which the vapors are no longer able to entrain the heavier of the catalyst particles, allowing the catalyst particles to fall back to the top end 110 of the elongated reaction tube 108. In this way, the freeboard zone 130 assists in separating the vapor from the catalyst.

The FCC reactor 102 may further comprise a cyclone 140. The freeboard zone 130 may be in fluid communication with the cyclone 140 through a conduit 142. The cyclone 140 may further comprise a product outlet 144 and a fines outlet 149 for ejecting the catalyst fines separated from the stream 146. The cyclone 140 may be designed to efficiently separate the remaining catalyst particles from the cracked hydrocarbons.

The cyclone 140 may operate under a combination of centrifugal force, gravity settling, and the specific design of the cyclone chamber.

The catalyst regenerator 202 may comprise a riser 208 having an inlet end 212 and an outlet end 210. The inlet end 212 of the riser 208 may be in fluid communication with the catalyst outlet 128 of the stripping unit 120. Conduit 127 may extend between the catalyst outlet 128 of the stripping unit 120 and the inlet end 212 of the riser 208 of the catalyst regenerator 202. The riser 208 may comprise further comprise an oxygen-containing gas inlet 222. The riser 208 may be operable to contact the used cracking catalyst with an oxygen-containing gas 224, which may cause combustion of coke deposits on the used catalyst. The catalyst regenerator 202 may further comprise a separator 230, which may be in fluid communication with and axially disposed above the riser 208. The separator 230 may be fluidly coupled to the catalyst inlet 118 of the FCC reactor 102 to transfer regenerated catalyst from the catalyst regenerator 202 back to the reaction zone 106 of the FCC reactor 102. The separator 230 may further comprise a gas outlet 232. The separator 230 may be operable to separate the regenerated cracking catalyst from the combustion gases and accumulate the regenerated cracking catalyst for distribution back to the catalyst inlet 118 of the FCC reactor 102.

Still referring to FIG. 1, in operation, the hydrocarbon feed 116 may be introduced to the reaction zone 106 through the feed inlet 114. The hydrocarbon feed 116 may move through the reaction zone 106 in the +Z direction (opposite that of gravity) toward the top end 110 of the elongated reaction tube 108. An effective amount of heated fresh or hot regenerated catalyst from the catalyst regenerator 202 may be conveyed to the reaction zone 106 through the catalyst inlet 118. Catalyst may enter the reaction zone below the product outlet 144. Without wishing to be bound by theory, it is believed that introducing the catalyst below the product outlet 144 may reduce the amount of catalyst entrained in the FCC effluent 146 exiting the FCC reactor 102. The heated fresh or hot regenerated catalyst composition particles from the catalyst regenerator 202 may be conveyed to the catalyst inlet 118 of the reaction zone 106 through the conduit 119, commonly referred to as a transfer line or standpipe. In embodiments, the system 101 may include a catalyst hopper (not shown) disposed between the catalyst regenerator 202 and the FCC reactor 102. The hopper may be operable to stabilize the temperature of the catalyst and uniformly distribute the catalyst into the reaction zone 106. Once introduced to the reaction zone 106, the catalyst may move in a direction from the catalyst inlet 118 in a downward direction toward the bottom end 112 of the elongated reaction tube 108. Contact of the hot catalyst with hydrocarbons from the hydrocarbon feed may cause at least a portion of the hydrocarbons to undergo cracking reactions to produce light olefins.

As the hydrocarbon feed 116 and the catalyst move counter-currently through the reaction zone 106, the hydrocarbon feed 116 may have an upward superficial velocity (opposite that of gravity) through a horizontal cross-section of the reaction zone 106, and the catalyst may have a downward superficial velocity (direction of gravity) through a horizontal cross-section of the reaction zone 106. For example, the hydrocarbon feed 116 flows from the feed inlet 114 proximate the bottom end 112 of the reaction zone 106 to the product outlet 144. Thus, the net flow of the hydrocarbon feed 116 moving through a horizontal cross-section of the FCC reactor 102 is in an upward direction (i.e., +Z direction), resulting in an upward superficial velocity. Likewise, the catalyst flows from the catalyst inlet 118 proximate the top end 110 of the reaction zone 106 to the catalyst outlet 128 in the stripping unit 120 of the FCC reactor 102, and the net flow of the catalyst moving through a horizontal cross-section of the FCC reactor 102 is in a downward direction (i.e., −Z direction), resulting in a downward superficial velocity. In embodiments, the upward superficial velocity of the hydrocarbon feed 116 and the downward superficial velocity of the catalyst results in a counter-current flow pattern between the hydrocarbon feed 116 and the catalyst. Thus, in embodiments, the hydrocarbon feed 116 and catalyst move with a counter-current flow regime. The flow of the hydrocarbon feed 116, catalyst, or both through the reaction zone 106 may approach plug flow behavior.

In embodiments, the catalyst-to-oil weight ratio in the reaction zone 106 may be from 5 to 100. The catalyst-to-oil weight ratio is equal to the mass flow rate of catalyst into the catalyst inlet 118 divided by the mass flow rate of the hydrocarbon feed 116 into the feed inlet 114. For example, the catalyst-to-oil ratio in the reaction zone 106 may be from 5 to 100, from 10 to 100, from 20 to 100, from 30 to 100, from 40 to 100, from 50 to 100, from 60 to 100, from 70 to 100, from 80 to 100, or even from 90 to 100. In further examples, the catalyst-to-oil ratio in the reaction zone 106 may be from 5 to 90, from 5 to 80, from 5 to 70, from 5 to 60, from 5 to 50, from 5 to 40, from 5 to 30, from 5 to 20, or even from 5 to 10. Without wishing to be bound by theory, it is believed that there is less constraint on catalyst-to-oil ratios suitable for use in the reaction zone 106 because the catalyst may flow through the reaction zone 106 by gravity instead of being transported through the reactor by the flow of hydrocarbons. Additionally, a high catalyst-to-oil ratio indicates a large amount of catalyst within the reaction zone 106, which is believed to lead to increased conversion of hydrocarbons in the hydrocarbon feed 116 to light olefins.

Without wishing to be bound by theory, it is believed that contacting the hydrocarbon feed 116 and the catalyst in a counter-current manner may prevent back-mixing of catalyst that may occur in in traditional riser reactors and may promote undesired side reactions that negatively affect the production of light olefins. Additionally, it is believed that contacting the hydrocarbon feed 116 and the catalyst in a counter-current manner may prevent core-annular flow through the reactor where the catalyst has high concentration near the reactor walls and a low concentration toward the center of the elongated reaction tube 108 where a majority of the hydrocarbon flow occurs. Generally, core-annular flow reduces the amount of contact between the catalyst and the hydrocarbon, and thus, may reduce the conversion of hydrocarbon feed to light olefins.

Without wishing to be bound by theory, it is also believed that counter-current flow may also result in increased yield of olefins by allowing the more reactive chemicals in the hydrocarbon feed 116 to contact less active catalyst, and less reactive chemicals from the hydrocarbon feed 116 to contact more active catalyst. Generally, the catalyst closer to the bottom end 112 of the reaction zone 106 has already contacted hydrocarbons near the top end 110 of the reaction zone 106. Thus, the catalyst near the bottom end 112 of the reaction zone 106 may be at least partially spent and may have a lower catalytic activity compared to the fresh or regenerated catalyst near the top end 110 of the reaction zone 106. Contacting the hydrocarbon feed 116 with a large amount of less active catalyst at the feed inlet proximate the bottom end 112 of the reaction zone may allow the more reactive chemicals in the hydrocarbon feed to undergo cracking reactions proximate the bottom end 112 of the reaction zone 106 while contacting the less active catalyst. This in turn allows the more active catalyst near the top end 110 of the reaction zone 106 to crack the less reactive chemicals in the hydrocarbon feed, increasing the yield of light olefins produced from the hydrocarbon feed.

In embodiments, the superficial velocity of the hydrocarbon feed 116 moving through the reaction zone 106 may be less than or equal to 3.0 m/s. In embodiments, the superficial velocity of the hydrocarbon feed 116 through the reaction zone may be less than or equal to 3.0 m/s, less than or equal to 2.0 m/s, less than or equal to 1.0 m/s, less than or equal to 0.9 m/s, less than or equal to 0.8 m/s, less than or equal to 0.7 m/s, less than or equal to 0.6 m/s, less than or equal to 0.5 m/s, or even less than or equal to 0.4 m/s. Without wishing to be bound by theory, it is believed that a superficial velocity of the hydrocarbon feed 116 less than or equal to 3.0 m/s within the reaction zone 106 may result in increased contact between the catalyst and the hydrocarbons, which may in turn lead to increased conversion of the hydrocarbon feed to light olefins.

To keep the superficial velocity of the hydrocarbon feed 116 within the desired range, the residence time of the hydrocarbons within the FCC reactor 102 may be controlled by the flow rate of the hydrocarbon feed or the pressure in the FCC reactor 102. In embodiments, the residence time of the hydrocarbon feed 116 within the FCC reactor 102 may be from 0.1 to 30 seconds. For example, the residence time of the hydrocarbon feed 116 within the FCC reactor 102 may be from 0.1 to 30 seconds, from 0.5 to 30 seconds, from 1 to 30 seconds, from 5 to 30 seconds, from 10 to 30 seconds, from 15 to 30 seconds, from 20 to 30 seconds, from 25 to 30 seconds, from 0.1 to 20 seconds, from 0.5 to 10 seconds, from 2 to 20 seconds, from 4 to 20 seconds, from 6 to 20 seconds, from 8 to 20 seconds, from 10 to 20 seconds, from 12 to 20 seconds, from 14 to 20 seconds, from 16 to 20 seconds, from 18 to 20 seconds, from 0.1 to 10 seconds, from 0.5 to 10 seconds, from 1 to 10 seconds, from 2 to 10 seconds, from 3 to 10 seconds, from 4 to 10 seconds, from 5 to 10 seconds, from 6 to 10 seconds, from 7 to 10 seconds, from 8 to 10 seconds, or even from 9 to 10 seconds. In further examples, the residence time of the hydrocarbon feed 116 in the reactor 100 may be from 0.1 to 9 seconds, from 0.1 to 8 seconds, from 0.1 to 7 seconds, from 0.1 to 6 seconds, from 0.1 to 5 seconds, from 0.1 to 4 seconds, from 0.1 to 3 seconds, from 0.1 to 2 seconds, or even from 0.1 to 1 second.

In embodiments, the temperature within the FCC reactor 102 may be from 400° C. to 750° C. to facilitate the cracking of hydrocarbon feed 116. In embodiments, the temperature within the FCC reactor 102 may be from 420° C. to 750° C., 460° C. to 750° C., from 500° C. to 750° C., from 540° C. to 750° C., from 580° C. to 750° C., from 620° C. to 750° C., from 660° C. to 750° C., or even from 700° C. to 750° C. In further examples, the temperature within the FCC reactor 102 may be from 420° C. to 710° C., from 420° C. to 670° C., from 420° C. to 630° C., from 420° C. to 590° C., from 420° C. to 550° C., or even from 420° C. to 510° C. In yet further embodiments, the temperature within the FCC reactor 102 may be from 440° C. to 720° C., from 480° C. to 680° C.

Still referring to FIG. 1, as the hydrocarbon feed 116 contacts the catalyst, at least a portion of the hydrocarbon feed 116 may be cracked to form cracked hydrocarbon fluids. In embodiments, the cracked hydrocarbon fluids may comprise light olefins and other reactions products. For example the cracked hydrocarbon fluids may comprise, ethylene, propylene, butenes, or combinations of these in addition to the other reactions products. In embodiments, the other reaction products may comprise dry gas, aromatics, naphtha, light cycle oil, heavy cycle oil, and even heavy oil. In embodiments, the cracked hydrocarbon fluids may comprise catalyst entrained within the cracked hydrocarbon fluids. The entrained catalyst may be separated from the cracked hydrocarbon fluids in the freeboard zone 130. In embodiments, the cracked hydrocarbon fluids comprising light olefins may be passed from top end 110 of the reaction zone 106 through the freeboard zone 130.

The freeboard zone 130 may increase in cross-sectional area such that it is operable to reduce the superficial velocity of any entrained catalyst within the cracked hydrocarbon fluids to fall back to the top end 110 of the reaction zone 106, thereby separating at least a portion of entrained catalyst from the cracked hydrocarbon fluids. The freeboard zone 130 may gradually increase in cross-sectional area from the top end 110 of the reaction zone 106 in the +Z direction, as seen in FIG. 1.

The freeboard zone 130 may have an inlet diameter at an inlet 133 of the freeboard 130 and an outlet diameter at the outlet 135 of the freeboard 130. The freeboard zone 130 may have a diameter ratio, where the diameter ratio is the ratio of the outlet diameter to the inlet diameter. For example, the freeboard zone 130 may have a diameter ratio from 1.5 to 5, from 1.5 to 4.5, from 1.5 to 4, from 1.5 to 3.5, from 1.5 to 3, from 1.5 to 2.5, from 1.5 to 2, from 2 to 5, from 2 to 4.5, from 2 to 4, from 2 to 3.5, from 2 to 3, from 2 to 2.5, from 2.5 to 5, from 2.5 to 4.5, from 2.5 to 4, from 2.5 to 3.5, from 2.5 to 3, from 3 to 5, from 3 to 4.5, from 3 to 4, from 3 to 3.5, from 3.5 to 5, from 3.5 to 4.5, from 3.5 to 4, from 4 to 5, from 4 to 4.5, or even from 4.5 to 5.

The freeboard zone 130 may have an inlet cross-sectional area at an inlet 133 of the freeboard 130 and an outlet cross-sectional area at the outlet 135 of the freeboard 130. The freeboard zone 130 may have a cross-sectional area ratio, where the cross-sectional area ratio is the ratio of the outlet cross-sectional area to the inlet cross-sectional area. The cross-sectional area ratio may be from 2.25 to 25. For example, the cross-sectional area ratio may be from 2.25 to 25, from 2.25 to 24, from 2.25 to 22, from 2.25 to 20, from 2.25 to 18, from 2.25 to 16, from 2.25 to 14, from 2.25 to 12, from 2.25 to 10, from 2.25 to 8, from 2.25 to 6, from 2.25 to 4, from 4 to 25, from 4 to 24, from 4 to 22, from 4 to 20, from 4 to 18, from 4 to 16, from 4 to 14, from 4 to 12, from 4 to 10, from 4 to 8, from 4 to 6, from 6 to 25, from 6 to 24, from 6 to 22, from 6 to 20, from 6 to 18, from 6 to 16, from 6 to 14, from 6 to 12, from 6 to 10, from 6 to 8, from 8 to 25, from 8 to 24, from 8 to 22, from 8 to 20, from 8 to 18, from 8 to 16, from 8 to 14, from 8 to 12, from 8 to 10, from 10 to 25, from 10 to 24, from 10 to 22, from 10 to 20, from 10 to 18, from 10 to 16, from 10 to 14, from 10 to 12, from 12 to 25, from 12 to 24, from 12 to 22, from 12 to 20, from 12 to 18, from 12 to 16, from 12 to 14, from 14 to 25, from 14 to 24, from 14 to 22, from 14 to 20, from 14 to 18, from 14 to 16, from 16 to 25, from 16 to 24, from 16 to 22, from 16 to 20, from 16 to 18, from 18 to 25, from 18 to 24, from 18 to 22, from 18 to 20, from 20 to 25, from 20 to 24, from 20 to 22, from 22 to 25, from 22 to 24, or even from 24 to 25.

As stated herein, the freeboard zone 130 increase in cross-sectional area such that it is operable to reduce the superficial velocity of any entrained catalyst within the cracked hydrocarbon fluids to fall back to the top end 110 of the reaction zone 106. The freeboard zone 130 may have an inlet velocity at the inlet 133 of the freeboard 130 and an outlet velocity and an outlet velocity at the outlet 135 of the freeboard. The freeboard zone 130 may have a velocity ratio, where the velocity ratio is the ratio of the outlet velocity to the inlet velocity. The velocity ratio may be from 1/25 to 1/2.25. For example, the velocity ratio may be from 1/25 to 1/2.25, from 1/25 to 1/3, from 1/25 to 1/5, from 1/25 to 1/7, from 1/25 to 1/9, from 1/25 to 1/11, from 1/25 to 1/13, from 1/25 to 1/15, from 1/25 to 1/17, from 1/25 to 1/19, from 1/25 to 1/21, from 1/25 to 1/23, from 1/23 to 1/2.25, from 1/23 to 1/3, from 1/23 to 1/5, from 1/23 to 1/7, from 1/23 to 1/9, from 1/23 to 1/11, from 1/23 to 1/13, from 1/23 to 1/15, from 1/23 to 1/17, from 1/23 to 1/19, from 1/23 to 1/21, from 1/21 to 1/2.25, from 1/21 to 1/3, from 1/21 to 1/5, from 1/21 to 1/7, from 1/21 to 1/9, from 1/21 to 1/11, from 1/21 to 1/13, from 1/21 to 1/15, from 1/21 to 1/17, from 1/21 to 1/19, from 1/19 to 1/2.25, from 1/19 to 1/3, from 1/19 to 1/5, from 1/19 to 1/7, from 1/19 to 1/9, from 1/19 to 1/11, from 1/19 to 1/13, from 1/19 to 1/15, from 1/19 to 1/17, from 1/17 to 1/2.25, from 1/17 to 1/3, from 1/17 to 1/5, from 1/17 to 1/7, from 1/17 to 1/9, from 1/17 to 1/11, from 1/17 to 1/13, from 1/17 to 1/15, from 1/15 to 1/2.25, from 1/15 to 1/3, from 1/15 to 1/5, from 1/15 to 1/7, from 1/15 to 1/9, from 1/15 to 1/11, from 1/15 to 1/13, from 1/13 to 1/2.25, from 1/13 to 1/3, from 1/13 to 1/5, from 1/13 to 1/7, from 1/13 to 1/9, from 1/13 to 1/11, from 1/11 to 1/2.25, from 1/11 to 1/3, from 1/11 to 1/5, from 1/11 to 1/7, from 1/11 to 1/9, from 1/9 to 1/2.25, from 1/9 to 1/3, from 1/9 to 1/5, from 1/9 to 1/7, from 1/7 to 1/2.25, from 1/7 to 1/3, from 1/7 to 1/5, from 1/5 to 1/2.25, from 1/5 to 1/3, or even from 1/3 to 1/2.25.

It is contemplated that the freeboard zone 130 may also include baffles and internals. The baffles and internals may be inserted into the freeboard zone 130 to promote gas-solid separation and aid in entrainment reduction. Additionally, vibrations may be applied to the baffles and internals to prevent catalyst particles from settling on and building up within the freeboard zone 130.

The cracked hydrocarbon fluids may then be passed through a conduit 142 to an additional separation unit, which may be a solid-fluid separator operable to separate solid particles from a fluid, such as a gas. Any suitable solid-fluid separation device, including a cyclone or series of cyclones, may be used to separate entrained catalyst fines from the cracked hydrocarbon fluids. Referring again to FIG. 1, in embodiments, a cyclone 140 may be in fluid communication with the freeboard zone 130 through the conduit 142. The cyclone 140 may receive the cracked hydrocarbon fluids and any remaining entrained catalyst fines at a high velocity. The cyclone 140 may subject the hydrocarbon fluids and any remaining entrained catalyst to centrifugal forces, causing the heavier entrained catalyst to move towards the outer wall of the cyclone 140 while the lighter cracked hydrocarbon fluids move towards the center of the cyclone 140. As a result, the entrained catalyst particles are effectively separated and collected at the bottom of the cyclone for recycling. The lighter cracked hydrocarbon fluids are passed out of the cyclone 140 through the product outlet 144 as the FCC effluent 146. The FCC effluent 146 may be passed to one or more downstream unit operations for further processing. The catalyst fines are separated out of the cyclone 140 through the catalyst fines outlet 149. The catalyst fines may be disposed of if too small or may be recycled back to the catalyst regenerator 202.

In embodiments, cracking the hydrocarbon feed 116 may produce spent catalyst. In embodiments, spent catalyst may comprise coke deposited on the catalyst, may have a reduced temperature compared to fresh or regenerated catalyst, or both. The coke may reduce the catalytic activity of the catalyst, and the spent catalyst may have reduced catalytic activity when compared to regenerated or fresh catalyst.

In embodiments, spent catalyst may pass from the bottom end 112 of the reaction zone 106 to the stripping unit 120. Steam may be passed to the stripping unit 120 through steam inlet 122. In the stripping unit 120, steam may contact the spent catalyst and strip at least a portion of the hydrocarbon feed 116 or cracked hydrocarbon fluids from the spent catalyst. After contacting the steam in the stripping unit 120, spent catalyst may be passed from the FCC reactor 102 to the catalyst regenerator 202 through the catalyst outlet 128. The stripping gases may be passed out of the stripping unit 120 via an outlet 131.

In embodiments, the spent catalyst may be passed from the stripping unit 120 to the catalyst regenerator 202 where the spent catalyst is regenerated to form a regenerated catalyst. The spent catalyst may enter the riser 208 through the catalyst outlet 128. In embodiments, the riser 208 may be in fluid communication with the stripping unit 120 of the FCC reactor 102 and the spent catalyst may be passed directly from the stripping unit 120 to the riser 208. In embodiments, the oxygen-containing gas 224 may be passed to the riser 208 through an oxygen-containing gas inlet 222 and the oxygen-containing gas 224 and spent catalyst travel up (e.g., in the +Z direction) the riser 208. In embodiments, the oxygen-containing gas 224 may be contacted with the spent catalyst, which may cause at least a portion of the coke on the spent catalyst to oxidize, removing the coke deposits and restoring activity to the spent catalyst to produce the regenerated catalyst. Oxidation of the coke deposits may also generate heat, which heats the regenerated catalyst to a temperature greater than the reaction temperature in the FCC reactor 102.

The regenerated catalyst and combustions gases may move from the riser 208 to the separator 230 of the regenerator 200. The combustion gases may include unreacted oxygen, carbon monoxide, water vapor, carbon dioxide, inert gases from the oxygen-containing gas stream, or other combustion gases. In embodiments, the riser 208 and separator 230 are adjacent to each other, and the regenerated catalyst and combustion gases move directly from the riser 208 to the separator 230. The separator 230 may be any suitable separation system for separating solids from fluids, such as separating the regenerated catalyst from the combustion gases. In embodiments, the separator 230 may include a cyclone separation system. In embodiments, a gas stream 234 may exit the separator 230 through a gas outlet 232. The regenerated catalyst may accumulate in a bottom portion of the separator 230. The regenerated catalyst may exit the bottom portion of the separator 230. In embodiments, the regenerated catalyst may passed directly from the bottom portion of the separator 230 to the FCC reactor 102. In embodiments, the separator 230 and reaction zone 106 may be in fluid communication with each other and the regenerated catalyst may be passed directly from the separator 230 of the catalyst regenerator 202 to the reaction zone 106 of the FCC reactor 102 through catalyst inlet 118. In embodiments, fresh catalyst may be added to catalyst in the catalyst inlet 118. In such embodiments, the catalyst may comprise both regenerated catalyst and fresh catalyst.

Now referring to FIG. 2, another FCC system 103 is depicted. The FCC system 103 may be similar or identical to the FCC system 101 of FIG. 1 except where described otherwise. In particular, the FCC system 103 may utilize a different structure and method to separate the entrained catalyst and the cracked hydrocarbon fluids passed from the top end 110 of the reaction zone 106 of the FCC reactor 102. As depicted in FIG. 2, the FCC system 103 may also perform additional cracking reactions in an FCC reactor 302 within a dense fluidized bed unit 150.

According to embodiments, the FCC reactor 302 may comprise a dense fluidized bed unit 150, which comprises a vessel 151 enclosing the top end 110 of the elongated reaction tube 108. The regenerated or fresh catalyst in the vessel 151 forms a dense fluidized bed 156. In embodiments, the dense fluidized bed 156 may have a dense bed fluidization regime. As described herein, a "dense bed fluidization regime" refers to a fluidization regime in which the fluidized bed has a clearly defined upper limit or surface to the dense bed. The dense bed fluidization regimes may include smooth fluidization, bubbling fluidization, slugging fluidization, or turbulent fluidization regimes. In embodiments, a fluidizing gas 158 may be injected into the dense fluidized bed unit 150. The fluidizing gas 158 may form bubbles between the solid particles of the dense fluidized bed 156. In the dense fluidized bed 156, the particle entrainment rate may be low, but may increase as the velocity of the fluidizing gas 158 flowing through the dense fluidized bed 156 increases. Without intending to be bound by theory, the flow rate of the fluidizing gas 158 may be used to control the flow rate of catalyst from the dense fluidized bed 156 to the reaction zone 106. In embodiments, catalyst may overflow from the dense fluidized bed 156 and fall to the reaction zone 106 through the top end 110 of the elongated reaction tube 108.

FIG. 2 depicts the dense fluidized bed 156 in packed-bed status before the fluidizing gas 158 is injected into the dense fluidized bed unit 150. While the dense fluidized bed 156 surrounds the top end 110 of the reaction zone 106 in FIG. 2, it should be understood that once the fluidizing gas 158 is injected into the dense fluidized bed 156, the dense fluidized bed 156 will expand and begin to discharge catalyst into the elongated reaction tube 108 and reaction zone 106. Once fluidization begins, the dense fluidized bed 156 will be above the top 110 of the reaction zone 106.

As the cracked hydrocarbon fluids pass through the reaction zone 106 to the product outlet 152, a portion of the cracked hydrocarbon fluids may be held up in the dense fluidized bed 156. Injection of the fluidizing gas 158 into the dense fluidized bed 156 may purge the cracked hydrocarbon fluids from the dense fluidized bed, effectively separating the cracked hydrocarbon fluids from the catalyst. The flow rate of the fluidizing gas 158 may be used to control the purge rate of the cracked hydrocarbon fluids.

In embodiments, the fluidizing gas 158 may comprise, steam, nitrogen, helium, argon, methane, or combinations of these. In embodiments, the fluidization gas 158 may include one or more hydrocarbon feeds, recycle streams, oxygenate streams, or combinations of these. It is also contemplated that the fluidizing gas 158 may comprise an additional hydrocarbon feed. Upon injecting the fluidization gas 158 into the dense fluidized bed 156, hydrocarbons from the additional hydrocarbon streams, recycle streams, oxygenate streams, or both included in the fluidization gas 158 may be contacted with the cracking catalyst in the dense fluidized bed 158 at a temperature sufficient to cause at least a portion of the hydrocarbons to under cracking reactions to produce additional reaction products, such as but not limited to light olefins, light aromatic compounds, or both. Injecting recycle stream or oxygenate streams into the dense fluidized bed 156 as a part of the fluidization gas 158 may increase the yield of light olefins from the reactor system.

The fluidized bed of catalyst 156 may assist in catalyst distribution into the FCC reactor 102, such as into the top end 110 of the elongated reaction tube 108. Now referring to FIG. 3, in embodiments, the dense fluidized bed 156 may further comprise a catalyst feed zone 312 and a perforated plate distributor 330. The catalyst discharge zone may be disposed axially above the perforated plate distributor 330. In embodiments, the catalyst may overflow from the dense fluidized bed 156 and fall through the catalyst feed zone 312 to a perforated plate distributor 330. The catalyst may overflow from the dense fluidized bed 156 into a conduit 420 and pass from the dense fluidized bed 156 to the perforated plate distributor 330 through conduit 420. In embodiments, the dense fluidized bed unit 150 may comprise a plurality of conduits 420 extending between the dense fluidized bed 156 and the perforated plate distributor 330. Catalyst may overflow from the dense fluidized bed 156 into the plurality of conduits 420 and pass from the dense fluidized bed 156 to the perforated plate distributor 330. The number of conduits 420 is not necessarily limited. The shapes and distributions of conduits 420 are not necessarily limited. In embodiments, the conduits 420 may be symmetric on a central vertical axis (e.g., in the +/−Y direction). In embodiments, the dense fluidized bed unit 150 may comprise from 1 to 50 conduits. In embodiments, the internal diameter of each conduit may be from 5 mm to 30 mm.

Figure 4:
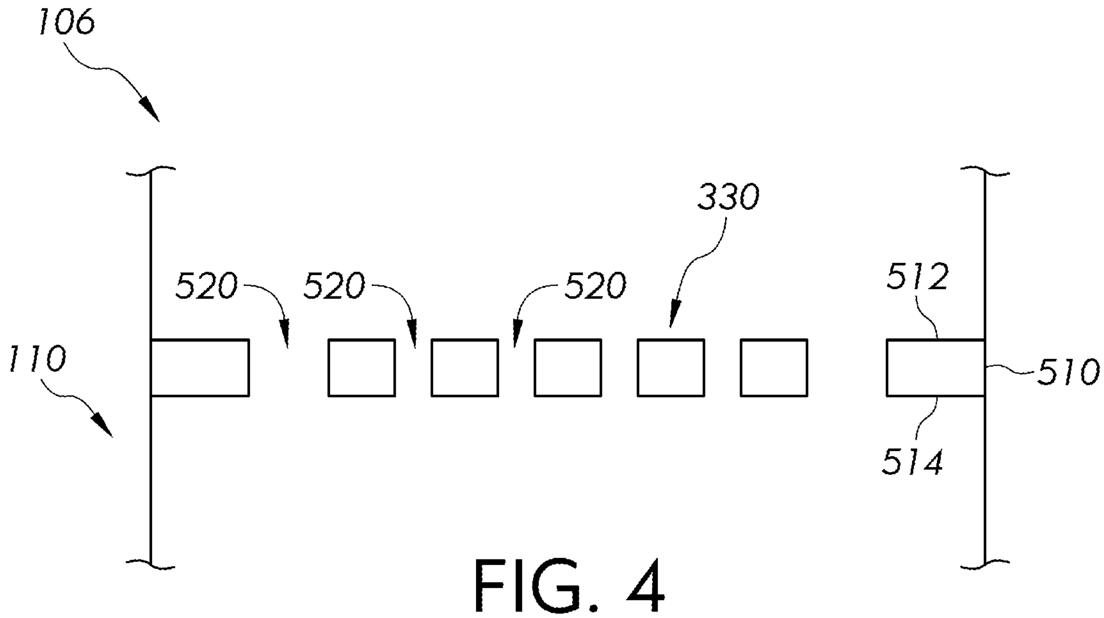
FIG. 4 schematically depicts a perforated plate distributor, according to embodiments shown and described in the present disclosure.

Referring now to FIG. 4, the perforated plate distributor 330 may comprise a plate 510 extending along a substantially horizontal cross-section of the reaction zone 106 of the FCC reactor 102 within the FCC system 103. As described herein, a "substantially horizontal cross-section" may be within 15°, 10°, 5°, or even 1° of horizontal. The plate 510 may have a first surface 512 and a second surface 514, the second surface 514 being opposite the first surface 512. The plate 510 may comprise a plurality of perforations 520. Each perforation may be an opening extending from the first surface 512 of the plate 510 to the second surface 514 of the plate 510. The perforations 520 may be sized such that the catalyst used in the FCC system 103 may pass through the perforations 520. The perforations 520 may be positioned in any suitable pattern or distribution on the plate 510 such that the catalyst is uniformly distributed to the reaction zone 106 of the FCC reactor 102 when the catalyst is passed through the perforated plate distributor 330. The perforations 520 may have any suitable cross-sectional shape. For example, without limitation, the perforations may have a circular, oval, or polygonal cross sectional shape, in a cross section parallel to the first surface 512 and the second surface 514 of the plate 510. In embodiments, the perforated plate distributor 330 may extend along the entirety of a substantially horizontal cross-section of the elongated reaction tube 108 such that substantially all of the catalyst entering the reaction zone 106 passes through the perforated plate distributor 330.

In embodiments, the plate 510 may have a thickness from 0.05 m to 0.5 m. The thickness of the plate 510 refers to the distance between the first surface 512 and the second surface 514 of the plate 510. For example, without limitation, the plate 510 may have a thickness from 0.05 m to 0.5 m, from 0.1 m to 0.5 m, from 0.15 m to 0.5 m, from 0.2 m to 0.5 m, from 0.25 m to 0.5 m, from 0.3 m to 0.5 m, from 0.35 m to 0.5 m, from 0.4 m to 0.5 m, from 0.45 m to 0.5 m, from 0.05 m to 0.45 m, from 0.05 m to 0.4 m, from 0.05 m to 0.35 m, from 0.05 m to 0.3 m, from 0.05 m to 0.25 m, from 0.05 m to 0.2 m, from 0.05 m to 0.15 m, from 0.05 m to 0.1 m, or any range or combination of ranges formed from these endpoints.

In embodiments, the perforations 520 may have a diameter of from 5 mm to 50 mm. In embodiments with non-circular perforations, the diameter refers to the diameter of the smallest circle circumscribing the perforation 520. In embodiments, the perforations 520 may have a diameter of from 5 mm to 50 mm, from 15 mm to 50 mm, from 25 mm to 50 mm, from 35 mm to 50 mm, from 45 mm to 50 mm, from 5 mm to 40 mm, from 5 mm to 30 mm, from 5 mm to 20 mm, from 5 mm to 10 mm, or any range or combination of ranges formed from these endpoints. In embodiments the perforations may each have substantially the same size. In embodiments, the perforations may have different sizes. In embodiments, the perforations may be arranged in a symmetric pattern on the plate 510. A distance between the perforations 520 is not necessarily limited. In embodiments, a distance between a perforation 520 and the next closest perforation 520 may be less than or equal to half of the diameter of the perforation 520. The distance between perforations 520 may be the shortest distance from the edge of one perforation 520 to the edge of another perforation 520.

EXAMPLES

The following non-limiting examples illustrate one or more features of the present disclosure. The examples are illustrative in nature, and should not be understood to limit the subject matter of the present disclosure.

Example 1: Co-Current Flow Conversion

In Example 1, a micro-activity testing (MAT) unit was used to determine the conversion and selectivity of a hydrocarbon stream in a co-current configuration using 1 g of fresh cracking catalyst. After the reactor was preheated to the desired reaction temperature under atmospheric pressure by inert gas, the crude oil (Table 1, 1.33 g) was fed by a syringe pump for an injection time of 75 seconds. The product stream was passed through a multiport valve at the bottom of the reactor to the receiving vessel, which was immersed in a cooling bath to separate the liquid products. All the gas phase products were sent and contained in a gas collector and analyzed by a Thermo Scientific Trace 1310 gas chromatograph (GC) with a MolSieve analytical column, thermal conductivity detectors (TCD), an Alumina plot column and flame ionization detectors (FID). The liquid product stream was analyzed according to the offline analytical test methods. In particular, the liquid product stream was analyzed by simulated distillation according to test method EN 15199-2 using the Agilent 7890 gas chromatograph. Coke is quantified after passing an air stream through the reactor at high temperatures to burn the coke into a mixture of carbon monoxide, carbon dioxide, and water, by passing through a calibrated infrared analyzer. The reaction products for Example 1 are provided in Table 2.

Example 2: Simulated Counter-Current Reactor

In Example 2, the effects of a counter-current flow reactor were simulated using the MAT unit with two catalyst beds, including an upper catalyst bed of used catalysts (0.75 g) and a lower catalyst bed with fresh catalysts (0.25 g). With a downward oil feeding above the top bed, the dual bed configuration provided a similar environment as in the counter-current downer reactor, where the oil first contacts the used catalysts in the upper catalyst bed and the partially cracked products interact with fresh catalysts in the lower catalyst bed downstream of the used catalysts. The same type of cracking catalyst was used for Example 1 and Example 2. The deactivated catalysts were obtained by running an experiment under the same conditions with fresh catalysts in the MAT reactor. The catalytic cracking performance of the simulated counter-current reactor was evaluated at 575° C. by comparison with the MAT unit with 1 g fresh catalyst. The reactor effluent was separated into gaseous and liquid components and analyzed as described in Example 1. The coke on the catalyst was evaluated according to the method described in Example 1. The product distributions are exhibited in Table 2 for gas composition, liquid analysis, and coke. The relations between olefins and paraffins production, and the propylene/ethylene ratio are also shown.

TABLE 1

| Physical properties of Arabian Extra Light Crude Oil | |
|---|---|
| Density at 25° C. (g/mL) | 0.83 |
| Sulfur (wt. %) | 0.9 |
| Simulated distillation (Gasoline/Diesel/Bottoms) (wt. %) | 38.57/29.98/31.45 |
| Paraffins/Isoparaffins/Olefins/Naphtenes/Aromatics (wt. %) | 37.91/29.89/2.88/16.8/12.5 |

TABLE 2

Comparison of Co-Current and Counter-Current Reactions

| Yield wt. (%) | Example 1 | Example 2 |
|---|---|---|
| $H_2$ | 0.05 | 0.04 |
| $CH_4$ | 1.36 | 1.28 |
| $C_2H_6$ | 1.48 | 1.43 |
| $C_2H_4$ | 2.81 | 2.84 |
| $C_3H_8$ | 0.87 | 0.97 |
| $C_3H_6$ | 5.53 | 6.21 |
| i-butane | 0.38 | 0.34 |
| n-butane | 0.28 | 0.33 |
| t-2-butene | 0.62 | 0.66 |
| 1-butene | 0.60 | 0.62 |
| i-butylene | 1.09 | 1.13 |
| c-2-butene | 0.42 | 0.44 |
| i-pentane | 0.09 | 0.07 |
| n-pentane | 0.04 | 0.04 |
| 1-3-butadiene | 0.08 | 0.05 |
| pentenes | 0.69 | 0.61 |
| Gasoline | 32.82 | 32.83 |
| Diesel | 31.79 | 31.97 |
| Bottoms | 17.56 | 16.67 |
| Coke | 1.5 | 1.5 |
| | Ratios | |
| Olefins/Paraffins | 2.63 | 2.81 |
| Propylene/Ethylene | 1.97 | 2.19 |

As seen in Table 2, similar yield distribution is achieved from the counter-current reactor as the MAT unit with a reduced amount of fresh catalysts, while the olefins/paraffins and propylene/ethylene ratios are higher. The decreased amount of bottoms in the liquid analysis verifies a higher crude oil conversion in the counter-current configuration. By using the counter-current reactor, a higher conversion was achieved with comparable gas and liquid yields to the original MAT unit by one-fourth of the fresh catalysts and shifted the reaction to be more catalytic-dominated with higher olefins/paraffins and propylene/ethylene ratios.

Example 3: Counter-Current Reactor With Catalyst Circulation and Dense Bed

Experiments were performed with a lab-scale, fully circulated fluidized bed reactor with a dense bed at the bottom and counter-current section. The catalysts moved in a downward direction with gravity through the counter-current downer reactor, and the crude oil was injected and flowed upward from a dense bed section in a counter-current contact pattern. The catalysts circulated continuously from the reactor to the regenerator at 675° C. to regenerate the catalyst by air flow, and to perform the reaction at 600° C. The total amount of catalyst in the loop (reactor, regenerator, transfer lines, stripper) is roughly around 300-500 g.

TABLE 3

| Circulated Catalyst with Counter Current Flow Reaction Data Yield wt. (%) | |
|---|---|
| $H_2$ | 1.0 |
| $CH_4$ | 4.7 |
| $C_2H_6$ | 4.3 |
| $C_2H_4$ | 11.3 |
| $C_3H_8$ | 5.7 |
| $C_3H_6$ | 15.1 |
| i-butane | 2.9 |
| n-butane | 1.3 |
| t-2-butene | 2.1 |
| 1-butene | 1.3 |
| cis-2-butene/isobutene | 4.0 |
| cis-2-butene/isobutene | 1.5 |
| i-pentane | 1.1 |
| pentane | 0.9 |
| 1-pentene | 0.1 |
| t-2-pentene | 1.1 |
| cis-2-pentene | 0.8 |
| i-hexane | 1.6 |
| n-hexane | 0.4 |
| Sum | 61.3 |
| C2= + C3= | 26.4 |
| C2= - C4= | 35.3 |
| Coke | 6.1 |
| Liquids | 32.6 |

As seen in Table 3, a light olefin yield of 35% is achieved from the counter-current reactor with a dense bed at the bottom.

Example 4: Simulated Comparison of Co-Current and Counter-Current Reactors

The hydrodynamics of catalyst in co-current and counter-current reactors is simulated in computational particle fluid dynamics (CPFD) software Barracuda Virtual Reactor (Houston, Texas).

Figure 5:
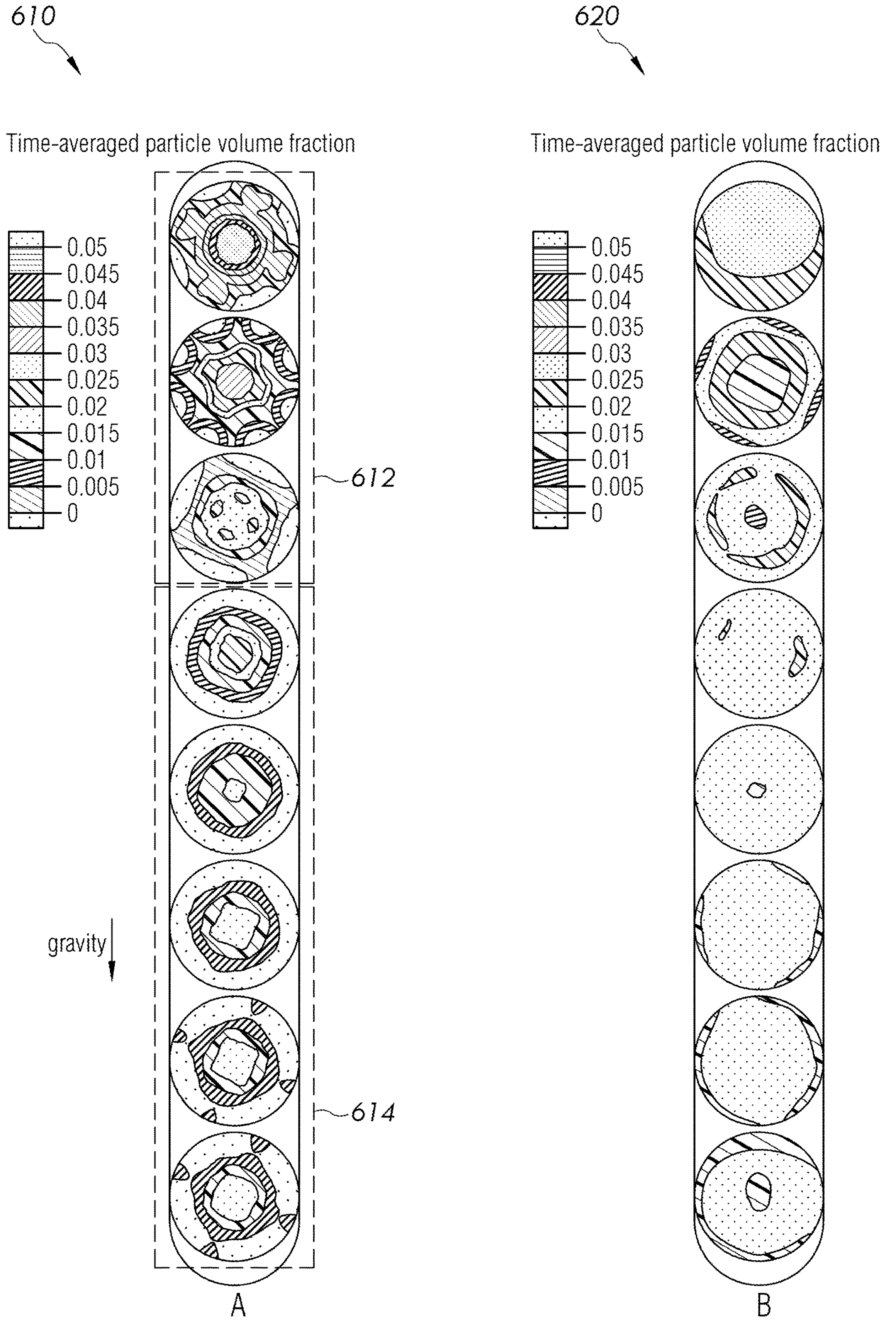
FIG. 5 graphically depicts simulated comparative models of catalyst distribution, according to embodiments shown and described in the present disclosure.
Figure 6:
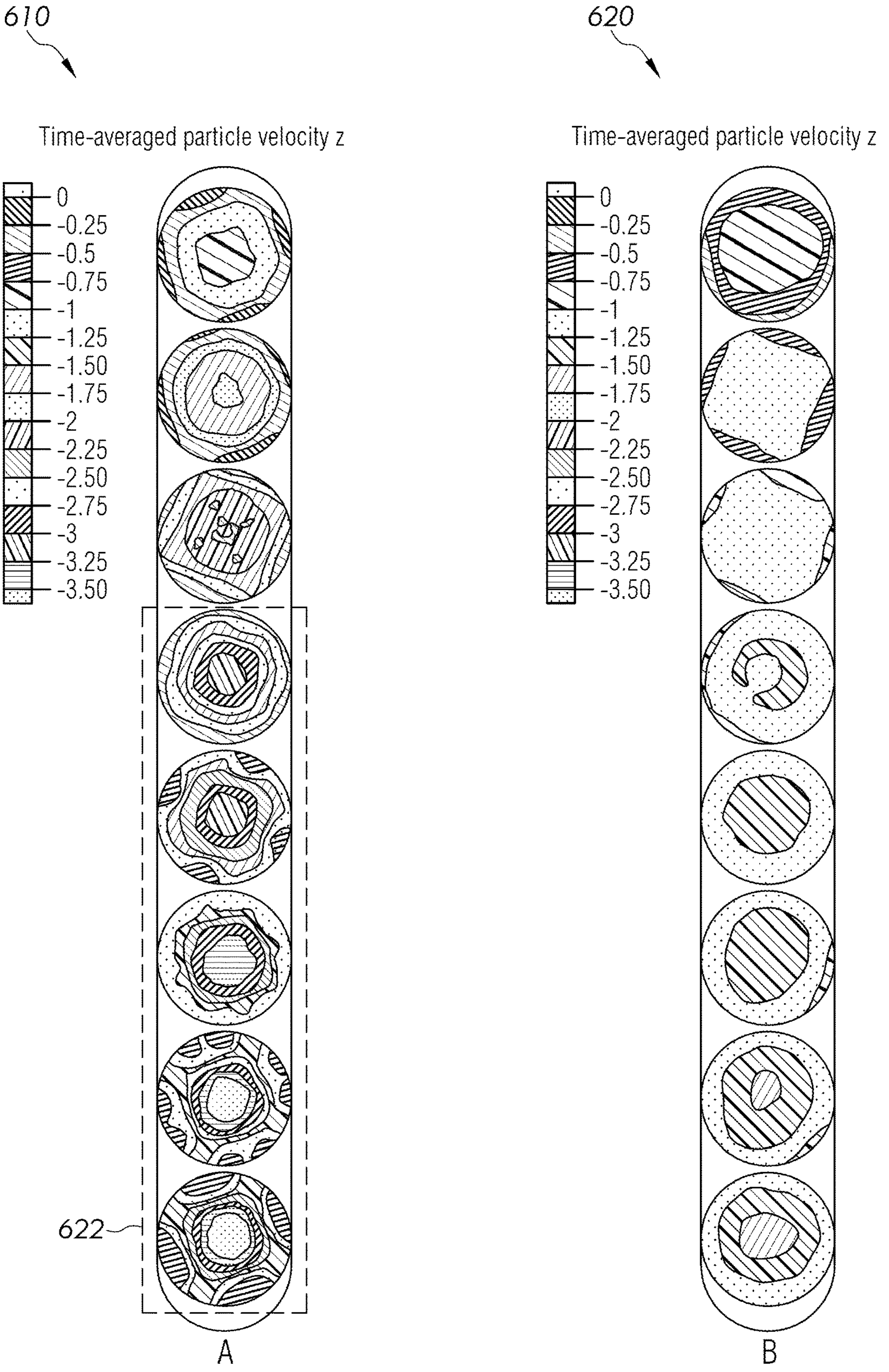
FIG. 6 graphically depicts simulated comparative models of catalyst distribution, according to embodiments shown and described in the present disclosure.

FIG. 5 displays the time-averaged radial solid holdup over eight equidistant planes. FIG. 6 displays the average particle velocity over eight equidistant planes. The co-current reactor is reactor 610, and the counter-current reactor is reactor 620. Both downer reactors were 25 mm in diameter and 1.8 m in height and operable to process 20 L/day of crude oil with 20% (w.t.) of steam fraction and a catalyst/oil ratio of 80 by a typical FCC catalyst (1500 kg $m^{-3}$, 75 μm) at the reaction condition of 650° C. and 1 atm.

FIG. 5 illustrates that the radial distribution of catalyst in reactor 610 (co-current mode) was non-uniform. In particular, catalyst near the center of the reactor experienced a greater holdup than catalyst near the edges of the reactor, with greater non-uniformity seen in acceleration zone 612 than acceleration zone 614. Non-uniformity of the catalyst holdup in the reactor may decrease the catalyst-reactant contacting efficiency. In contrast, reactor 620 (counter-current mode) benefits from the opposite moving directions of gas and particles and displays more uniformly distributed particles throughout most of the reactor. In particular, more evenly distributed catalyst is seen on the outer edges of the reactor 620 than reactor 610.

FIG. 6 is consistent with FIG. 5. Specifically, FIG. 6 illustrates that reactor 610 (co-current mode) experienced higher velocity near the center of the reactor than the edges of the reactor, particularly in acceleration zone 622. In contrast, reactor 620 (counter-current mode) displays a more uniform increase in velocity across each cross-section.

Figure 7:
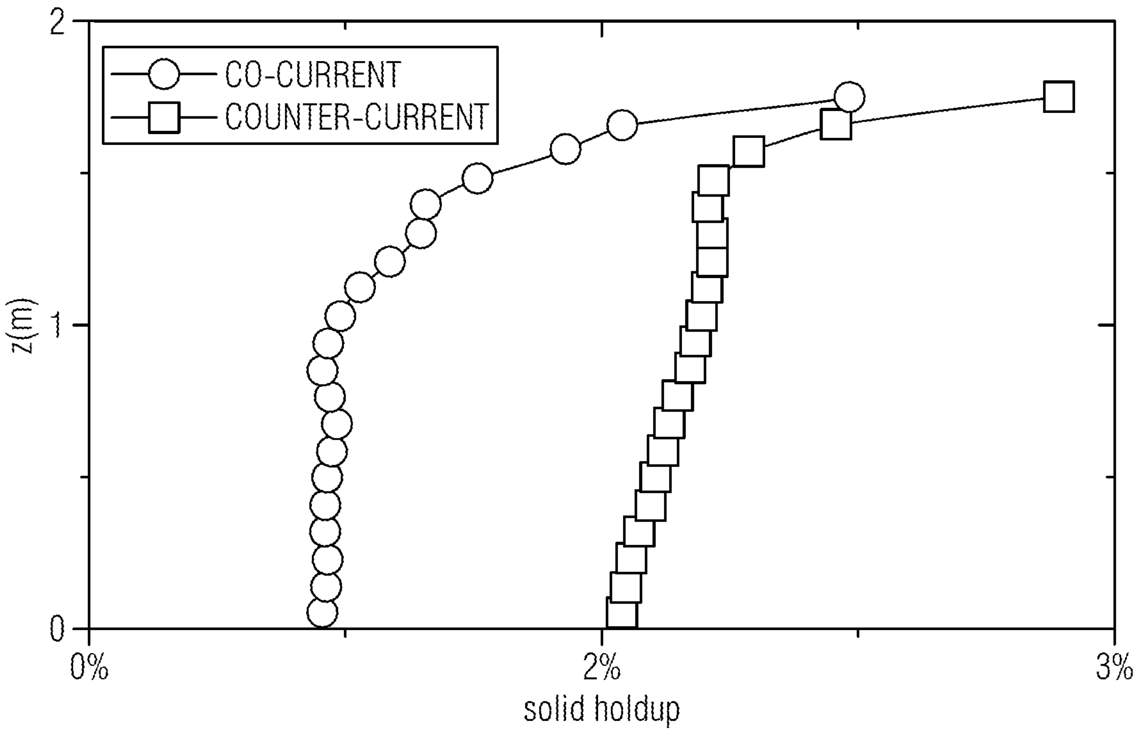
FIG. 7 is a comparative graph of catalyst holdup along reactor length, according to embodiments shown and described in the present disclosure.
Figure 8:
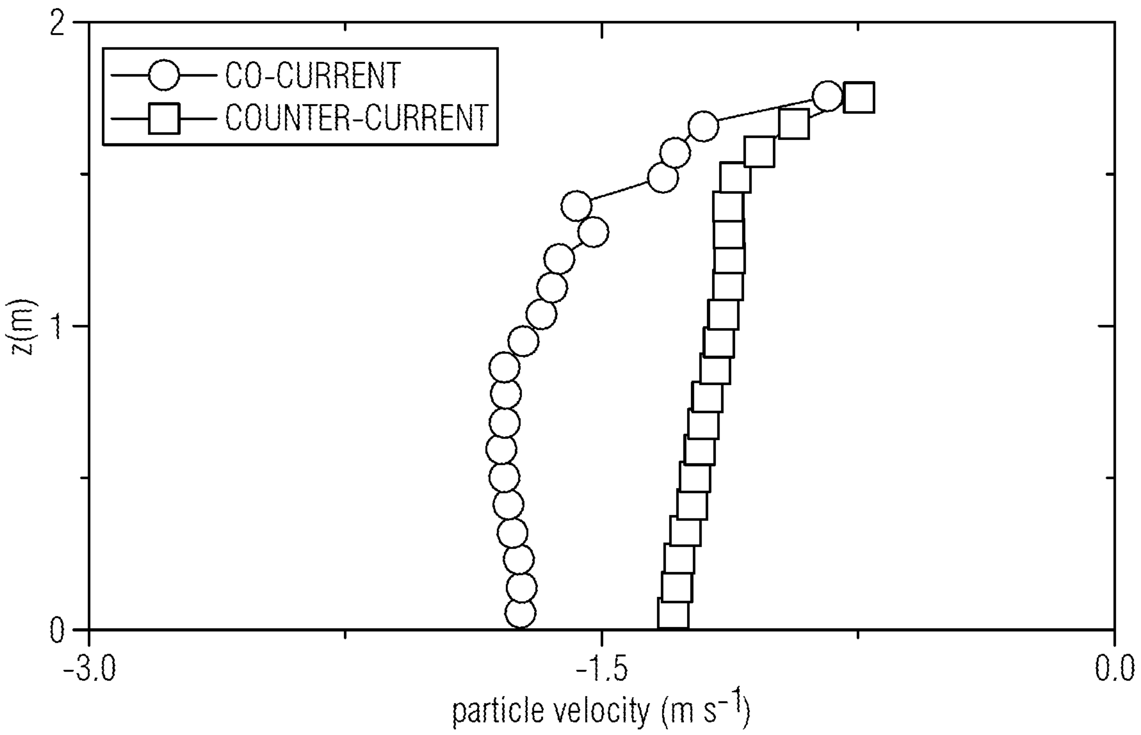
FIG. 8 is a comparative graph of catalyst velocity along reactor length, according to embodiments shown and described in the present disclosure.

FIG. 7 illustrates the axial solid holdup of reactors 610 and 620 by the time-averaged (from 10 s to 20 s) data of 20 isometric planes (from 0.05 m to 1.75 m) along each reactor. FIG. 8 illustrates the particle velocity of reactors 610 and 620 by the area-averaged data of 20 isometric planes (from 0.05 m to 1.75 m) along the reactor. When taken together, FIGS. 7 and 8 illustrate that reactor 620 (counter-current mode) demonstrated highly improved solid holdup (from less than 1% to more than 2%) with a lower particle velocity (from 1.74 to 1.29 m/s) at the developed zone, and decreases the acceleration section (from 0.6 to 0.3 m).

Figure 9:
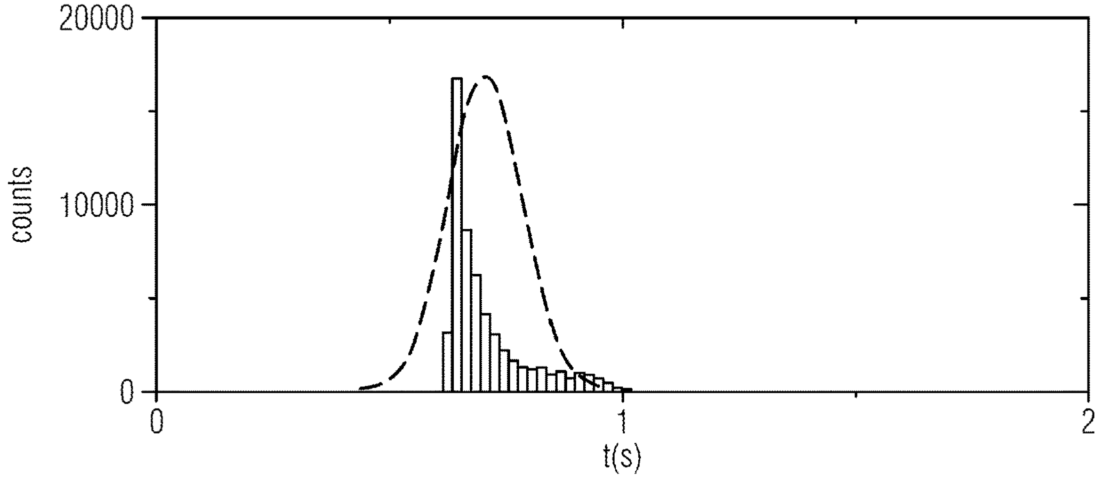
FIG. 9 is a histogram of catalyst residence time as a function of time for a co-current reactor.
Figure 10:
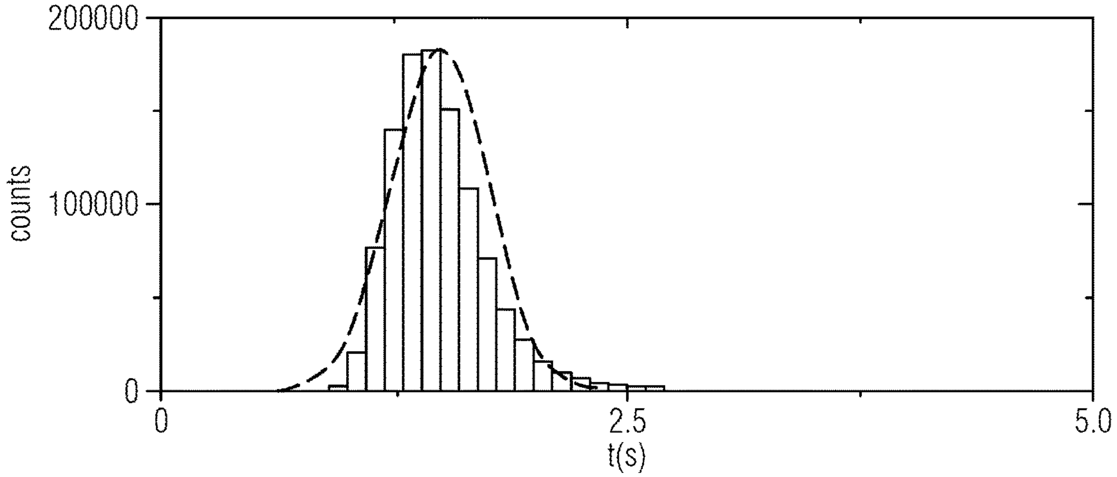
FIG. 10 is a histogram of catalyst residence time as a function of time for a counter-current reactor, according to embodiments shown and described in the present disclosure.
Figure 11:
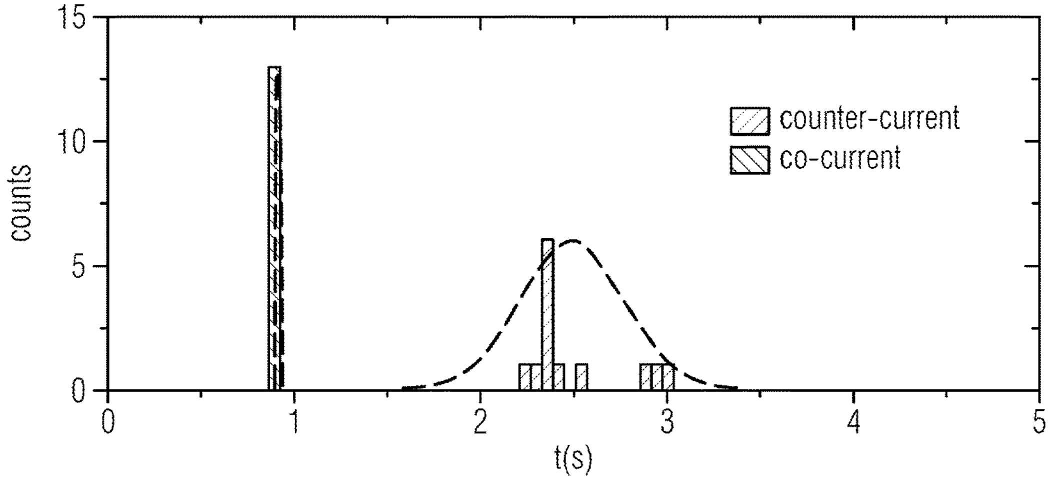
FIG. 11 is a histogram of gas residence time as a function of time for both co-current and counter-current reactors, according to embodiments shown and described in the present disclosure.

FIG. 9 illustrates the solid residence time distribution of the co-current operating mode in a histogram. FIG. 10 illustrates the solid residence time distribution of the counter-current operating mode in a histogram. FIG. 11 illustrates the gas residence time of both co-current and counter-current operating mode in a histogram. When taken together, FIGS. 9, 10, and 11 demonstrate that under the same reaction conditions with identical reactor sizes, the average solid residence time of the counter-current mode is twice the co-current, and the average gas residence time of the counter-current operation is three times the co-current. Nevertheless, both the solid and gas in both operating modes display a sharp and narrow distribution within 3 s. The relative longer gas-solid contact time from the counter-current reactor may lead to a further reactor design with shorter length, decreasing the capital investment.

Additionally, it may be observed that the co-current downer is not fully utilized with a core-shell solid distribution under ultra-fast residence time, leading to non-uniform gas-solid contacting and the risk of feed by-passing. Although the counter-current downer displays higher residence time distribution of both solid and gas, the improved and uniform gas-solid contact pattern demonstrates its potentiality for processing hydrocarbons to petrochemicals, such as light olefins.

In a first aspect of the present disclosure, a fluidized catalytic cracking (FCC) system for fluidized catalytic cracking of hydrocarbons to produce light olefin includes an FCC reactor and a catalyst regenerator, wherein the FCC reactor comprises: a reaction zone comprising an elongated reaction tube that is vertically oriented and has a top end and a bottom end; a feed inlet proximate the bottom end of the reaction zone; a product outlet proximate a top end of the reaction zone; a catalyst inlet proximate the top end of the reaction zone; a stripping unit disposed axially below the feed inlet and in fluid communication with the bottom end of the reaction zone, the stripping unit comprising a steam inlet and a catalyst outlet; and a freeboard zone disposed axially above the catalyst inlet and in fluid communication with the top end of the reaction zone; wherein: the reactor system is configured to introduce a hydrocarbon feed to the reaction zone through the feed inlet and a catalyst to the reaction zone through the catalyst inlet such that the catalyst contacts the hydrocarbon feed to produce cracked hydrocarbon fluids, the cracked hydrocarbon fluids have a net upward superficial velocity through the reaction zone; the catalyst has a net downward superficial velocity through the reaction zone; the net downward superficial velocity of the catalyst is counter-current relative to the net upward superficial velocity of the cracked hydrocarbon fluids; and the freeboard zone is configured to reduce a superficial velocity of the cracked hydrocarbon fluids at the top end of the reaction zone, which causes catalyst entrained in the cracked hydrocarbon fluids to fall back to the top end of the reaction zone, thereby separating at least a portion of entrained catalyst from the cracked hydrocarbon fluids.

A second aspect of the present disclosure may include the first aspect, wherein the freeboard zone is in fluid communication with a cyclone; and the cyclone is operable to separate the cracked hydrocarbon fluids from entrained catalyst to produce an FCC effluent; wherein: the catalyst comprises spent catalyst, regenerated catalyst, or a combination thereof; and the FCC effluent comprises one or more of ethylene, propylene, or butene.

A third aspect of the present disclosure may include either the first or second aspect, wherein the superficial velocity of the hydrocarbon feed in the reaction zone is 3.0 m/s or less.

A fourth aspect of the present disclosure may include any of the first through third aspects, wherein the hydrocarbon feed comprises crude oil.

A fifth aspect of the present disclosure may include any of the first through fourth aspects, wherein a catalyst to oil ratio in the reaction zone is from 5 to 100.

A sixth aspect of the present disclosure may include any of the first through fifth aspects, wherein a residence time of the hydrocarbon feed within the reactor is from 0.1 to 30 seconds.

A seventh aspect of the present disclosure may include any of the first through sixth aspects, wherein the catalyst regenerator comprises: a riser in fluid communication with the reaction zone at the catalyst outlet; and a separator fluidly coupled to the reaction zone at the catalyst inlet, wherein the separator is in fluid communication with and adjacent to the riser; wherein: the catalyst regenerator is configured to introduce spent catalyst from the catalyst outlet to the riser and form a regenerated catalyst and pass the regenerated catalyst to the reaction zone through the catalyst inlet.

An eighth aspect of the present disclosure many include any of the first through seventh aspects, wherein the freeboard zone comprises: an inlet diameter; and an outlet diameter, wherein a diameter ratio of the outlet diameter to the inlet diameter is from 1.5 to 5.

A ninth aspect of the present disclosure many include any of the first through eighth aspects, wherein the freeboard zone comprises: an inlet cross-sectional area; and an outlet cross-sectional area, wherein a cross-sectional area ratio of the outlet cross-sectional area to the inlet cross-sectional area is from 2.25 to 25.

A tenth aspect of the present disclosure many include any of the first through ninth aspects, wherein the freeboard zone comprises an inlet velocity; and an outlet velocity, wherein a velocity ratio of the outlet velocity to the inlet velocity is from $\frac{1}{25}$ to 1/2.25.

In an eleventh aspect of the present disclosure, a fluidized catalytic cracking (FCC) system for fluidized catalytic cracking of hydrocarbons to produce light olefins includes an FCC reactor and a catalyst regenerator, wherein the FCC reactor comprises: a reaction zone comprising an elongated reaction tube that is vertically oriented and has a top end and a bottom end; a feed inlet proximate the bottom end of the reaction zone; a catalyst inlet proximate a top end of the reaction zone; a stripping unit disposed axially below the feed inlet and in fluid communication with the bottom end of the reaction zone, the stripping unit comprising a steam inlet and a catalyst outlet; and a dense fluidized bed unit comprising a vessel enclosing the top end of the elongated reaction tube; wherein: the catalyst in the vessel forms a dense fluidized bed of solid particles; the FCC reactor is configured to introduce a hydrocarbon feed to the reaction zone through the feed inlet and a catalyst to the reaction zone through the catalyst inlet such that the catalyst contacts the hydrocarbon feed to produce cracked hydrocarbon fluids, wherein the catalyst comprises solid particles; cracked hydrocarbon fluids have a net upward superficial velocity through the reaction zone; the catalyst comprises solid particles and has a net downward superficial velocity through the reaction zone; the net downward superficial velocity of the catalyst is counter-current relative to the net upward superficial velocity of the hydrocarbons; the dense fluidized bed unit is configured to inject a fluidizing gas such that bubbles are formed within the solid particles of the dense fluidized bed of solid particles, which causes the catalyst to overflow from the dense fluidized bed of solid particles into the reaction zone.

A twelfth aspect of the present disclosure may include the eleventh aspect, wherein the dense fluidized bed unit houses a catalyst feed zone, and a perforated plate distributor, wherein the perforated plate distributor comprises: a plate extending along a horizontal cross-section of the elongated reaction tube, the plate comprising: a first surface; a second surface, wherein the second surface is opposite the first surface; and a plurality of perforations, wherein each of the plurality of perforations is an opening extending from the first surface of the plate to the second surface of the plate, and wherein: the perforations are configured such that the catalyst is uniformly distributed to the reaction zone when the catalyst passes through the perforated plate distributor.

A thirteenth aspect of the present disclosure may include either the eleventh or twelfth aspects, wherein the fluidizing gas comprises, steam, nitrogen, helium, argon, or methane.

An fourteenth aspect of the present disclosure may include any of the eleventh through thirteenth aspects, wherein the fluidizing gas has a superficial velocity of less than or equal to 5 m/s.

A fifteenth aspect of the present disclosure may include any of the eleventh through fourteenth aspects, wherein the dense fluidized bed of solid particles is operable to purge the cracked hydrocarbon fluids from the dense fluidized bed of solid particles, thereby separating the cracked hydrocarbon fluids from entrained catalyst.

A sixteenth aspect of the present disclosure may include any of the eleventh through fifteenth aspects, wherein a portion of the hydrocarbon feed is present in the dense fluidized bed of catalyst; and the dense fluidized bed of catalyst is operable to crack a portion of the hydrocarbon feed.

A seventeenth aspect of the present disclosure may include any of the eleventh through sixteenth aspects, wherein the catalyst regenerator comprises: a riser in fluid communication with the reaction zone at the catalyst outlet; and a separator fluidly coupled to the reaction zone at the catalyst inlet, wherein the separator is in fluid communication with and adjacent to the riser; wherein the catalyst regenerator is configured to introduce spent catalyst from the catalyst outlet to the riser and form a regenerated catalyst and pass the regenerated catalyst to the reaction zone through the catalyst inlet.

In an eighteenth aspect of the present disclosure, a method for cracking hydrocarbons to produce light olefins comprises introducing a hydrocarbon feed into a feed inlet of a fluidized catalytic cracking (FCC) reactor; introducing a catalyst into a catalyst inlet of the FCC reactor, wherein the FCC reactor comprises: a reaction zone comprising an elongated reaction tube that is vertically oriented and has a top end and a bottom end; a stripping unit disposed axially below the feed inlet and in fluid communication with the bottom end of the reaction zone, the stripping unit comprising a steam inlet and a catalyst outlet; a freeboard zone disposed axially above the catalyst inlet and in fluid communication with the top end of the reaction zone; contacting the catalyst with the hydrocarbon feed in the reaction zone to produce cracked hydrocarbon fluids and spent catalyst, wherein the catalyst has a net downward superficial velocity through the reaction zone and the cracked hydrocarbon fluids have a net upward superficial velocity through the reaction zone; passing the cracked hydrocarbon fluids and at least a portion of the spent catalyst through the freeboard zone which is operable to reduce the superficial velocity of the spent catalyst such that a portion of the spent catalyst is at least partially separated from the hydrocarbon fluids to form an FCC effluent; and passing the FCC effluent out of the FCC reactor through a product outlet.

A nineteenth aspect of the present disclosure may include the eighteenth aspect, further comprising: passing the cracked hydrocarbon fluids from the freeboard zone to a cyclone, wherein the cyclone is operable to further separate the FCC effluent from catalyst, wherein the catalyst comprises spent catalyst, regenerated catalyst, or a combination thereof.

A twentieth aspect of the present disclosure may include either the eighteenth or nineteenth aspects, further comprising: passing the spent catalyst to the stripping unit, wherein the spent catalyst comprises hydrocarbons; passing steam into the steam inlet of the stripping unit; and contacting the spent catalyst with steam to strip at least a portion of the hydrocarbons from the spent catalyst.

A twenty-first aspect of the present disclosure may include the twentieth aspect, further comprising passing the spent catalyst to a catalyst regenerator, wherein the catalyst regenerator comprises: a riser in fluid communication with the reaction zone at the catalyst outlet; and a separator fluidly coupled to the reaction zone at the catalyst inlet, wherein the separator is in fluid communication with and adjacent to the riser; regenerating the spent catalyst to form a regenerated catalyst; and passing the regenerated catalyst to the reaction zone through the catalyst inlet.

A twenty-second aspect of the present disclosure may include any of the eighteenth through twenty-first aspects, wherein the hydrocarbon feed comprises crude oil.

A twenty-third aspect of the present disclosure may include any of the eighteenth through twenty-second aspects, wherein the FCC effluent comprises one or more of ethylene, propylene, or butene.

It is noted that any two quantitative values assigned to a property may constitute a range of that property, and all combinations of ranges formed from all stated quantitative values of a given property are contemplated in this disclosure.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific aspects, it is noted that the various details of such aspects should not be taken to imply that these details are essential components of the aspects. Rather, the claims appended hereto should be taken as the sole representation of the breadth of the present disclosure and the corresponding scope of the various aspects described in this disclosure. Further, it will be apparent that modifications and variations are possible without departing from the scope of the appended claims.

What is claimed is:

1. A fluidized catalytic cracking (FCC) system for fluidized catalytic cracking of hydrocarbons to produce light olefins, the FCC system comprising an FCC reactor and a catalyst regenerator, wherein the FCC reactor comprises:

a reaction zone comprising an elongated reaction tube that is vertically oriented and having a top end and a bottom end;

a feed inlet proximate the bottom end of the reaction zone;

a product outlet proximate the top end of the reaction zone;

a catalyst inlet proximate the top end of the reaction zone;

a stripping unit disposed axially below the feed inlet and in fluid communication with the bottom end of the reaction zone, the stripping unit comprising a steam inlet and a catalyst outlet; and a freeboard zone disposed axially above the catalyst inlet and in fluid communication with the top end of the reaction zone;

wherein:

the reactor system is configured to introduce a hydrocarbon feed to the reaction zone through the feed inlet and a catalyst to the reaction zone through the catalyst inlet such that the catalyst contacts the hydrocarbon feed to produce cracked hydrocarbon fluids, the cracked hydrocarbon fluids have a net upward superficial velocity through the reaction zone;

the catalyst has a net downward superficial velocity through the reaction zone;

the net downward superficial velocity of the catalyst is counter-current relative to the net upward superficial velocity of the cracked hydrocarbon fluids; and the freeboard zone is configured to reduce a superficial velocity of the cracked hydrocarbon fluids at the top end of the reaction zone, which causes catalyst entrained in the cracked hydrocarbon fluids to fall back to the top end of the reaction zone, thereby separating at least a portion of entrained catalyst from the cracked hydrocarbon fluids.

2. The system of claim 1, wherein:

the freeboard zone is in fluid communication with a cyclone; and the cyclone is operable to separate the cracked hydrocarbon fluids from entrained catalyst to produce an FCC effluent;

wherein:

the catalyst comprises spent catalyst, regenerated catalyst, or a combination thereof; and the FCC effluent comprises one or more of ethylene, propylene, or butene.

3. The system of claim 1, wherein the superficial velocity of the hydrocarbon feed in the reaction zone is 3.0 m/s or less.

4. The system of claim 1, wherein the hydrocarbon feed comprises crude oil.

5. The system of claim 1, wherein a catalyst to oil ratio in the reaction zone is from 5 to 100.

6. The system of claim 1, wherein a residence time of the hydrocarbon feed within the reactor is from 0.1 to 30 seconds.

7. The system of claim 1, wherein the catalyst regenerator comprises:

a riser in fluid communication with the reaction zone at the catalyst outlet; and a separator fluidly coupled to the reaction zone at the catalyst inlet, wherein the separator is in fluid communication with and adjacent to the riser;

wherein:

the catalyst regenerator is configured to introduce spent catalyst from the catalyst outlet to the riser and form a regenerated catalyst and pass the regenerated catalyst to the reaction zone through the catalyst inlet.

8. A method for cracking hydrocarbons to produce light olefins, the method comprising:

introducing a hydrocarbon feed into a feed inlet of a fluidized catalytic cracking (FCC) reactor;

introducing a catalyst into a catalyst inlet of the FCC reactor, wherein the FCC reactor comprises:

a reaction zone comprising an elongated reaction tube that is vertically oriented and having a top end and a bottom end, wherein the feed inlet is located proximate the bottom end of the reaction zone and the catalyst inlet is located proximate the top end of the reaction zone;

a stripping unit disposed axially below the feed inlet and in fluid communication with the bottom end of the reaction zone, the stripping unit comprising a steam inlet and a catalyst outlet;

a freeboard zone disposed axially above the catalyst inlet and m fluid communication with the top end of the reaction zone;

contacting the catalyst with the hydrocarbon feed in the reaction zone to produce cracked hydrocarbon fluids and spent catalyst, wherein the catalyst has a net downward superficial velocity through the reaction zone and the cracked hydrocarbon fluids have a net upward superficial velocity through the reaction zone;

passing the cracked hydrocarbon fluids and at least a portion of the spent catalyst through the free board zone which is operable to reduce the superficial velocity of the spent catalyst such that a portion of the spent catalyst is at least partially separated from the hydrocarbon fluids to form an FCC effluent; and passing the FCC effluent out of the FCC reactor through a product outlet, wherein the product outlet is located proximate the top end of the reaction zone.

9. The method of claim 8, further comprising:

passing the cracked hydrocarbon fluids from the freeboard zone to a cyclone, wherein the cyclone is operable to further separate the FCC effluent from catalyst, wherein the catalyst comprises spent catalyst, regenerated catalyst, or a combination thereof.

10. The method of claim 8, further comprising:

passing the spent catalyst to the stripping unit, wherein the spent catalyst comprises hydrocarbons;

passing steam into the steam inlet of the stripping unit; and contacting the spent catalyst with steam to strip at least a portion of the hydrocarbons from the spent catalyst.

11. The method of claim 10, further comprising passing the spent catalyst to a catalyst regenerator, wherein the catalyst regenerator comprises:

a riser in fluid communication with the reaction zone at the catalyst outlet; and a separator fluidly coupled to the reaction zone at the catalyst inlet, wherein the separator is in fluid communication with and adjacent to the riser;

regenerating the spent catalyst to form a regenerated catalyst; and passing the regenerated catalyst to the reaction zone through the catalyst inlet.

12. The method of claim 8, wherein the hydrocarbon feed comprises crude oil.

13. The method of claim 8, wherein the FCC effluent comprises one or more of ethylene, propylene, or butene.

* * * * *